US011523792B2

(12) United States Patent
Forbes et al.

(10) Patent No.: US 11,523,792 B2
(45) Date of Patent: *Dec. 13, 2022

(54) METHODS AND SYSTEMS FOR AN ADAPTIVE MULTI-ZONE PERFUSION SCAN

(71) Applicant: GE Precision Healthcare LLC, Milwaukee, WI (US)

(72) Inventors: Ryan Forbes, Hartland, WI (US); Michael Sarju Vaz, Milwaukee, WI (US); Bradley Gabrielse, Brookfield, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 160 days.

This patent is subject to a terminal disclaimer.

(21) Appl. No.: 17/010,507

(22) Filed: Sep. 2, 2020

(65) Prior Publication Data
US 2021/0128097 A1    May 6, 2021

Related U.S. Application Data

(63) Continuation-in-part of application No. 16/672,314, filed on Nov. 1, 2019, now Pat. No. 11,341,636.

(51) Int. Cl.
*A61B 6/00*    (2006.01)
*G16H 50/20*   (2018.01)
(Continued)

(52) U.S. Cl.
CPC .............. *A61B 6/545* (2013.01); *A61B 6/481* (2013.01); *A61B 6/507* (2013.01); *A61B 6/5217* (2013.01);
(Continued)

(58) Field of Classification Search
CPC ......... A61B 6/032; A61B 6/481; A61B 6/504; A61B 6/507; A61B 6/5217; A61B 6/545;
(Continued)

(56) References Cited

U.S. PATENT DOCUMENTS 5,400,378 A    3/1995  Toth
6,023,494 A    2/2000  Senzig et al.
(Continued)

FOREIGN PATENT DOCUMENTS

CN    101277648 A    10/2008

OTHER PUBLICATIONS

"The ONE Guides—4D Neurological Imaging," Cannon Medical Systems USA Website, Available Online at https://us.medical.canon/download/aq-one-club-guide-4d-neuro-imaging, Available Online at Early as Jan. 2010, 16 pages.
(Continued)

*Primary Examiner* — Katrina R Fujita
(74) *Attorney, Agent, or Firm* — McCoy Russell LLP

(57) ABSTRACT

Methods and systems are provided for adaptive scan control. In one embodiment, a method includes processing acquired projection data of a monitoring area of a subject to measure a first contrast signal of a contrast agent administered to the subject via a first injection, initializing a contrast scan of the subject according to a fallback scan prescription, determining when each of a plurality of zones of the contrast scan are estimated to occur based on the contrast signal, generating a personalized scan prescription for the contrast scan based on when each of the plurality of zones are estimated to occur, and performing the contrast scan according to the personalized scan prescription after a second injection of the contrast agent.

19 Claims, 11 Drawing Sheets

(51) Int. Cl.
   *G16H 30/40* (2018.01)
   *G16H 50/50* (2018.01)
   *G16H 40/40* (2018.01)
   *G16H 50/70* (2018.01)
   *G01R 33/563* (2006.01)
   *G01R 33/56* (2006.01)

(52) U.S. Cl.
   CPC .............. *G16H 30/40* (2018.01); *G16H 40/40* (2018.01); *G16H 50/20* (2018.01); *G16H 50/50* (2018.01); *G16H 50/70* (2018.01); *G01R 33/5601* (2013.01); *G01R 33/56366* (2013.01)

(58) Field of Classification Search
   CPC .............. G01R 33/481; G01R 33/5601; G01R 33/56366; G16H 30/40; G16H 40/40; G16H 50/20; G16H 50/50; G16H 50/70
   See application file for complete search history.

(56) References Cited

U.S. PATENT DOCUMENTS

| | | | |
|---|---|---|---|
| 6,236,706 | B1 | 5/2001 | Hsieh |
| 6,256,368 | B1 | 7/2001 | Hsieh et al. |
| 6,891,918 | B2 | 5/2005 | Drummond et al. |
| 7,145,982 | B2 | 12/2006 | Ikeda et al. |
| 7,983,460 | B2 | 7/2011 | Licato et al. |
| 9,327,143 | B2 | 5/2016 | Gillece et al. |
| 9,486,176 | B2 | 11/2016 | Goyal |
| 9,517,042 | B2 | 12/2016 | Hsieh et al. |
| 9,622,717 | B2 | 4/2017 | Londt et al. |
| 10,349,909 | B2 | 7/2019 | Okerlund et al. |
| 2013/0066198 | A1* | 3/2013 | Grant ............. A61B 6/486 600/431 |
| 2016/0078619 | A1* | 3/2016 | Hsieh ............. A61B 6/545 378/4 |
| 2017/0086772 | A1 | 3/2017 | Vaz et al. |
| 2017/0209113 | A1 | 7/2017 | Jackson et al. |
| 2018/0049714 | A1 | 2/2018 | Nett |
| 2019/0231288 | A1 | 8/2019 | Profio et al. |

OTHER PUBLICATIONS

Hinzpeter, R. et al., "CT Angiography of the Aorta: Contrast Timing by Using a Fixed versus a Patient-specific Trigger Delay," University of Zurich Open Repository and Archive Website, Available Online at https://www.zora.uzh.ch/id/eprint/170529/1/radiol.2019182223.pdf, Available as Early as May 2019, 10 pages.

Lewis, C. et al., "Methods and Sytems for Protocol Management," U.S. Appl. No. 16/553,028, filed Aug. 27, 2019, 59 pages.

Vaz, M. et al., "Methods and Systems for Timing a Second Contrast Bolus," U.S. Appl. No. 16/672,261, filed Nov. 1, 2019, 84 pages.

Vaz, M. et al., "Methods and Systems for an Adaptive Multi-Phase Angiography Scan," U.S. Appl. No. 16/672,281, filed Nov. 1, 2019, 85 pages.

Vaz, M. et al., "Methods and Systems for an Adaptive Five-Zone Perfusion Scan," U.S. Appl. No. 16/672,314, filed Nov. 1, 2019, 85 pages.

Vaz, M. et al., "Methods and Systems for a Single-Bolus Angiography and Perfusion Scan," U.S. Appl. No. 16/672,336, filed Nov. 1, 2019, 85 pages.

Vaz, M. et al., "Methods and Systems for an Adaptive Four-Zone Perfusion Scan," U.S. Appl. No. 16/672,350, filed Nov. 1, 2019, 85 pages.

Vaz, M. et al., "Methods and Systems for an Adaptive Perfusion Scan," U.S. Appl. No. 16/698,291, filed Nov. 27, 2019, 43 pages.

* cited by examiner

METHODS AND SYSTEMS FOR AN ADAPTIVE MULTI-ZONE PERFUSION SCAN

RELATED APPLICATIONS

The present application is a continuation-in-part of U.S. application Ser. No. 16/672,314, entitled "METHODS AND SYSTEMS FOR AN ADAPTIVE MULTI-ZONE PERFUSION SCAN" and filed on Nov. 1, 2019, the entire contents of which are hereby incorporated by reference for all purposes.

FIELD

Embodiments of the subject matter disclosed herein relate to non-invasive diagnostic imaging, and more particularly, to real-time adaptive contrast imaging.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures).

For emergency room (ER) stroke management, time is critical to determine a proper course of treatment. For every minute a large vessel ischemic stroke is untreated, the average patient loses 1.9 million neurons. For each hour in which a treatment fails, the patient loses as many neurons as it does in almost 3.6 years of normal aging. Current standards of care require two contrast boli for separate CT angiography (CTA) and CT perfusion (CTP) studies. Further, prior to performing CTA and CTP studies, typical methods first perform a timing bolus scan, wherein a small contrast bolus is administered to a patient and subsequent contrast levels within the patient are monitored to generate a CTP/CTA scan prescription personalized to the patient. However, the timing bolus scan alone takes five minutes, and performing CTA and CTP studies separately requires five to seven minutes between acquisitions to allow contrast washout.

BRIEF DESCRIPTION

This summary introduces concepts that are described in more detail in the detailed description. It should not be used to identify essential features of the claimed subject matter, nor to limit the scope of the claimed subject matter.

In one aspect, a method can include processing acquired projection data of a monitoring area of a subject to measure a first contrast signal of a contrast agent administered to the subject via a first injection, initializing a contrast scan of the subject according to a fallback scan prescription, determining when each of a plurality of zones of the contrast scan are estimated to occur based on the contrast signal, generating a personalized scan prescription for the contrast scan based on when each of the plurality of zones are estimated to occur, and performing the contrast scan according to the personalized scan prescription after a second injection of the contrast agent.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
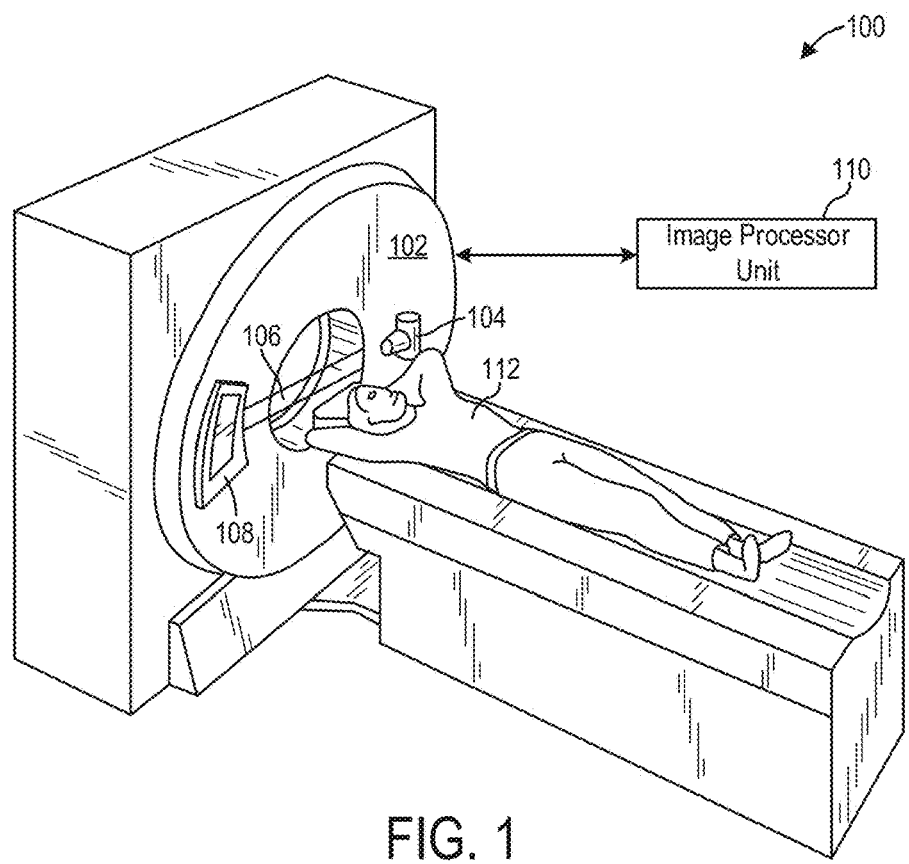
FIG. 1 shows a pictorial view of an imaging system, according to an embodiment.

Embodiments of the present disclosure will now be described, by way of example, with reference to the FIGS. 1-16, which relate to various embodiments for personalized, adaptive contrast imaging. Some diagnostic imaging protocols, such as protocols to diagnose acute stroke in a patient, include one or more contrast scans, where a contrast agent is administered to the patient prior to the diagnostic imaging scan. These diagnostic imaging protocols may include two contrast scans, such as a computed tomography (CT) angiography (CTA) scan followed by a CT perfusion (CTP) scan. In a CTA followed by a CTP (or in a CTP followed by a CTA), the decision of when to administer the second contrast agent bolus may be challenging, and if timed incorrectly, may result in non-diagnostic images and/or undesired patient outcomes. For example, if the second contrast agent bolus is administered too soon after the first contrast scan, diagnostic image quality of images acquired during the second contrast scan may be degraded due to venous contrast contamination from the first contrast agent bolus. However, if the second contrast agent bolus is administered too late after the first contrast scan, patient outcome (e.g., life expectancy, quality of life) may be impacted.

Thus, according to embodiments disclosed herein, personalized, adaptive contrast scans may be performed when no prior knowledge of the patient's contrast agent response is available. The adaptive contrast scans described herein may adjust aspects of the scan parameters (e.g., temporal acquisition rate) at one or more time points (referred to as zone transitions) that are identified based on the patient's individual contrast agent kinetics, such as the amount of time from contrast agent injection until various inflection points/time points of interest on the patient's arterial inflow function (AIF) curve and venous outflow function (VOF) curve, including but not limited to a venous peak and a venous return to baseline.

The contrast scan may be carried out according to a scan prescription that is set based on a predefined scan protocol. A lead technologist, a radiologist, and/or one or more additional clinicians/administrators may set various parameters for the pre-defined scan protocol in advance via an adaptive scan protocol graphical user interface (GUI). The adaptive scan protocol GUI may allow the lead technologist and/or other personnel to divide the contrast scan into zones, and set different scan parameters (such as temporal acquisition rate, also known as temporal sampling rate, x-ray source current, etc.) for each selected zone. The timing of when each zone is to occur may be set by the lead technologist based on patient events, such as the individual patient's hemodynamics/contrast agent response, which may be determined based on information obtained from a prior contrast scan and/or on the fly as the contrast scan progresses. Further, the lead technologist may set a fallback prescription that is used when the scan cannot be personalized/adapted.

During execution of a selected contrast scan protocol to image a patient with an imaging system (e.g., CT system), the operator/technologist of the imaging system may select the appropriate predefined scan protocol. The adaptive scan protocol GUI may be displayed to the operator, allowing the operator to confirm or, if necessary, change the preset scan parameters. The progress of the scan may be displayed via a run-time GUI, including (at least in some examples) a visual representation of the scan prescription in the form of a real-time, personalized representation of the patient's contrast agent response curve.

To determine the patient's individual contrast agent kinetics, a contrast agent signal may be measured during the previous scan and/or an initial portion of the contrast scan, and the contrast signal may comprise a measured contrast level in a monitoring region of the patient (e.g., a brain of the patient, an artery of the patient, a vein of the patient, etc.). This contrast agent signal may be entered as input to a machine learning (ML) model that may output an estimated arterial inflow function (AIF) curve, an estimated tissue uptake curve (TUC), and/or an estimated venous outflow function (VOF) curve (and/or time points of interest from the AIF and VOF curves, such as an arterial peak, a venous peak, and/or a venous return to baseline). Based on the output of the ML model, the timing of the one or more zone transitions may be identified and adjustments to the scan parameters (e.g., temporal sampling rate) may be made at the zone transitions. In doing so, patient x-ray radiation dose may be reduced and/or scan duration may be shortened while still acquiring high quality diagnostic images to support patient diagnosis.

However, in some patients, it may be challenging to identify the estimated AIF curve and the estimated VOF curve (and/or time points of interest from the AIF and VOF curves), as some patients may exhibit contrast agent kinetics that cannot be associated (e.g., by the ML model) with specific AIF and/or VOF curves in a time frame under which such protocol adaptation may be beneficial. Thus, the scan prescription described herein may initialize to the fallback, worst case scenario scan prescription that may overscan the patients but also ensure high quality diagnostic images for all patients even if the estimated contrast signal curves cannot be determined. Then, if the contrast signal curves can be estimated, the fallback scan prescription may be adapted on the fly, as discussed above.

Figure 2:
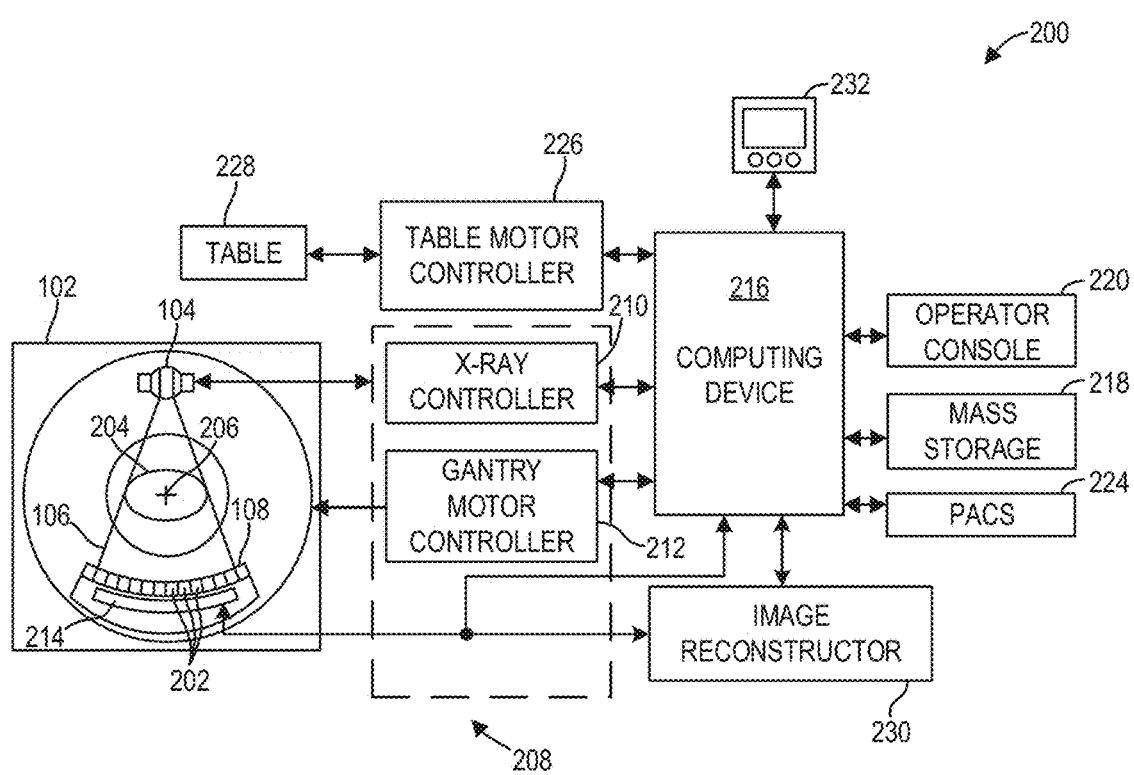
FIG. 2 shows a block schematic diagram of an exemplary imaging system, according to an embodiment.
Figure 3:
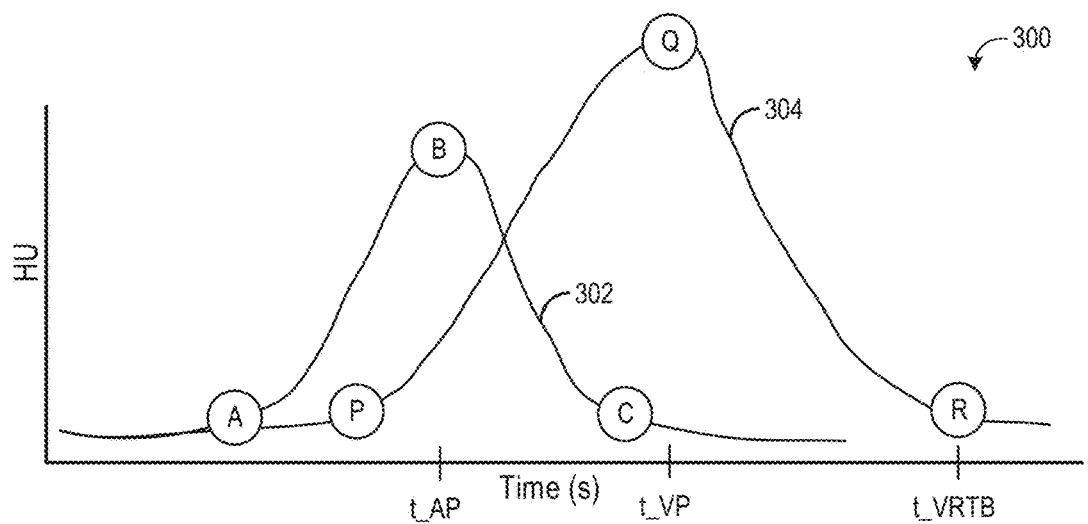
FIG. 3 shows a graph illustrating an example arterial inflow function (AIF) curve and an example a venous outflow function (VOF) curve generated during a contrast scan.
Figure 4:
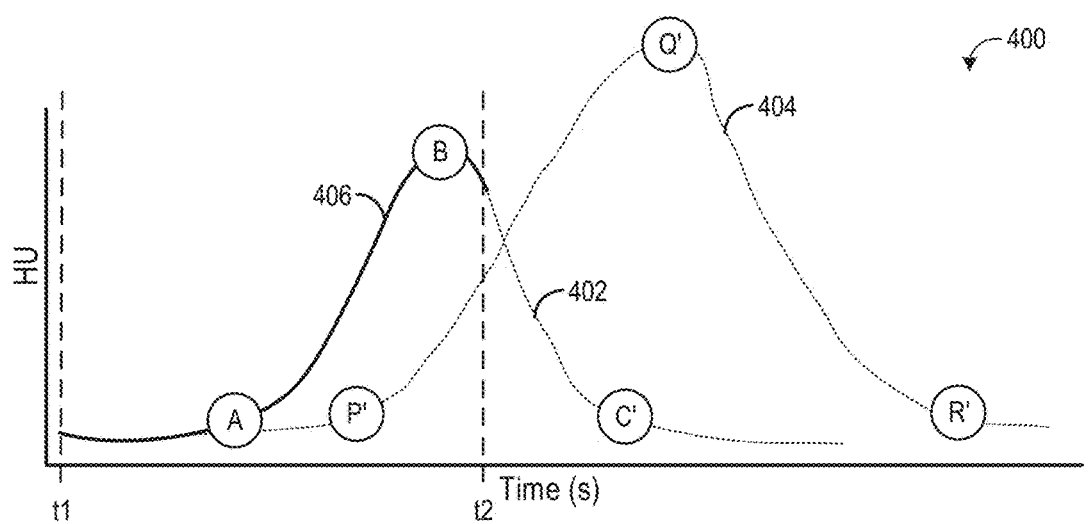
FIG. 4 shows a graph illustrating an estimated AIF curve and an estimated VOF curve generated according to an embodiment of the disclosure.
Figure 5:
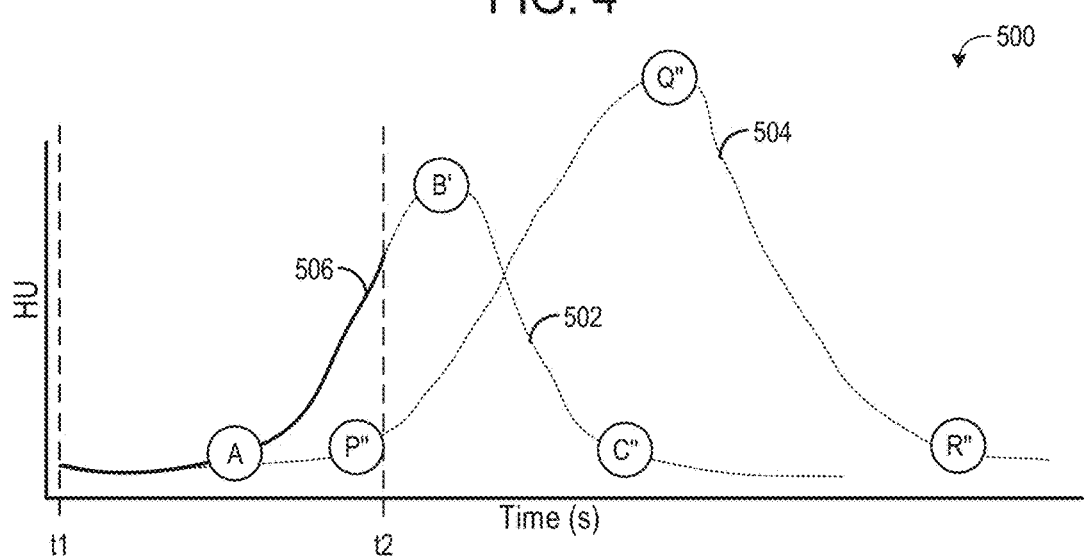
FIG. 5 shows a graph illustrating an estimated AIF curve and an estimated VOF curve generated according to another embodiment of the disclosure.
Figure 6:
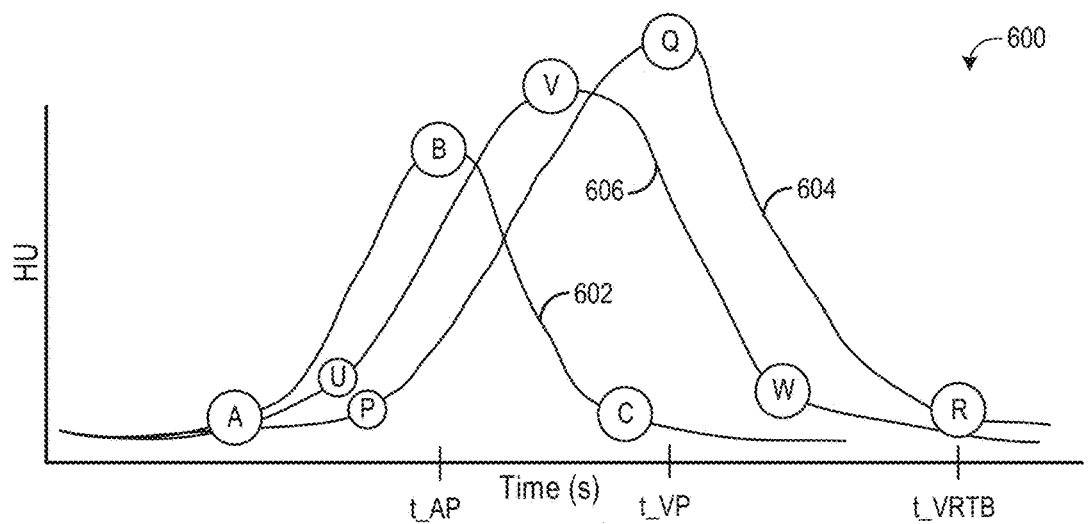
FIG. 6 shows a graph illustrating an example AIF curve, an example VOF curve, and an example tissue uptake curve (TUC) generated during a contrast scan.
Figure 7:
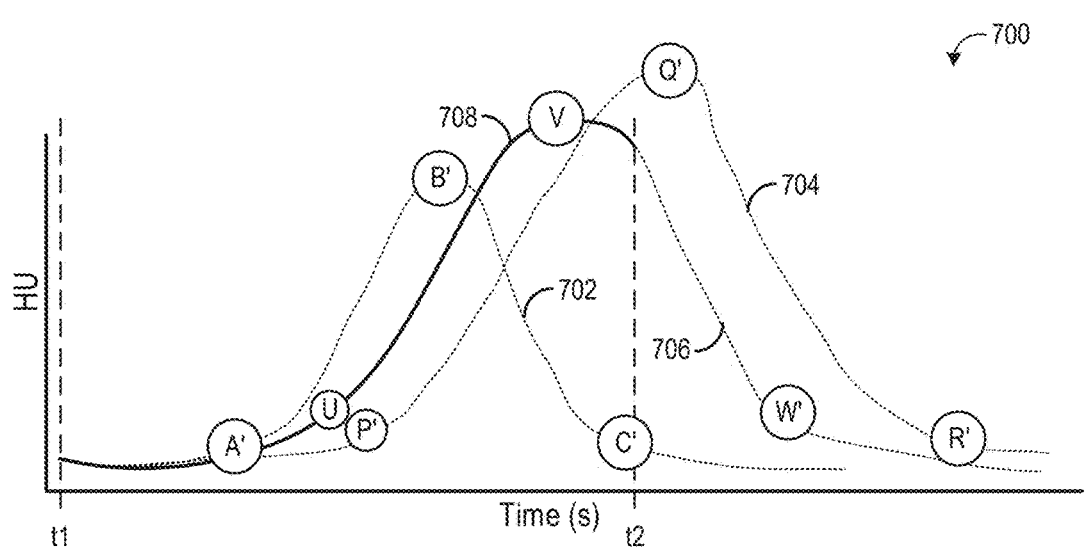
FIG. 7 shows a graph illustrating an estimated AIF curve, an estimated VOF curve, and an estimated TUC generated according to an embodiment of the disclosure.
Figure 8:
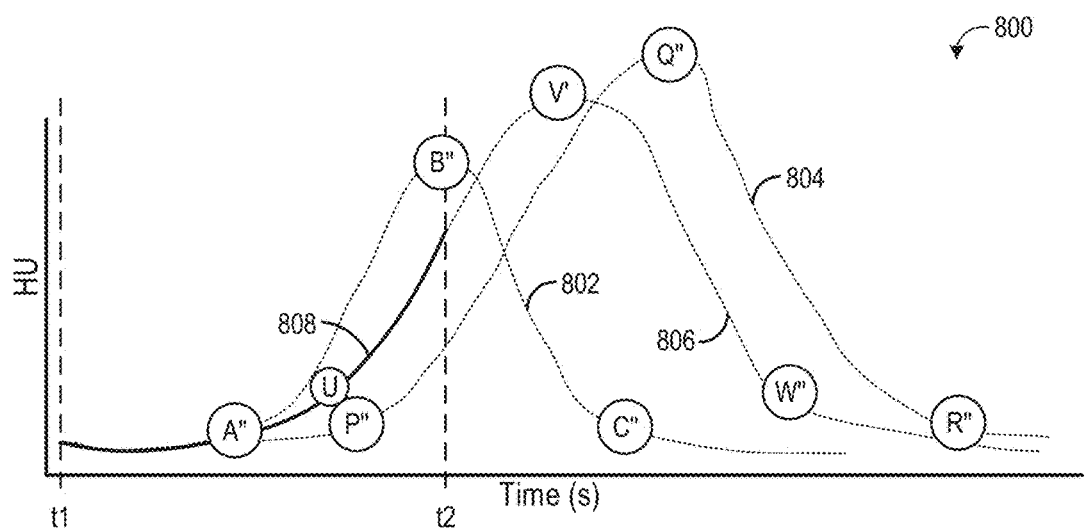
FIG. 8 shows a graph illustrating an estimated AIF curve, an estimated VOF curve, and an estimated TUC generated according to another embodiment of the disclosure.

An example of a computed tomography (CT) imaging system that may be used to perform the contrast scans in accordance with the present techniques is provided in FIGS. 1 and 2. As described above, the adaptation of the contrast scans may be dependent on the AIF and/or VOF curves of the contrast agent, which vary from patient to patient. FIG. 3 shows example AIF and VOF curves for a patient. A portion of the AIF curve may be directly measured prior to a first contrast scan commencing or during the first portion of the first contrast scan, and this portion may be used as input to a model to estimate the remaining AIF curve and the VOF curve for the patient, as shown in FIGS. 4 and 5. As another example, rather than measuring the AIF, tissue uptake of the contrast agent may be measured for a duration, and this measured portion of the tissue uptake curve (TUC) may be entered into a model to estimate the AIF and VOF curves. FIG. 6 shows example AIF, TUC, and VOF curves, while FIGS. 7 and 8 show example portions of the TUC that may be measured and used as input to estimate the AIF and VOF curves.

Figure 9:
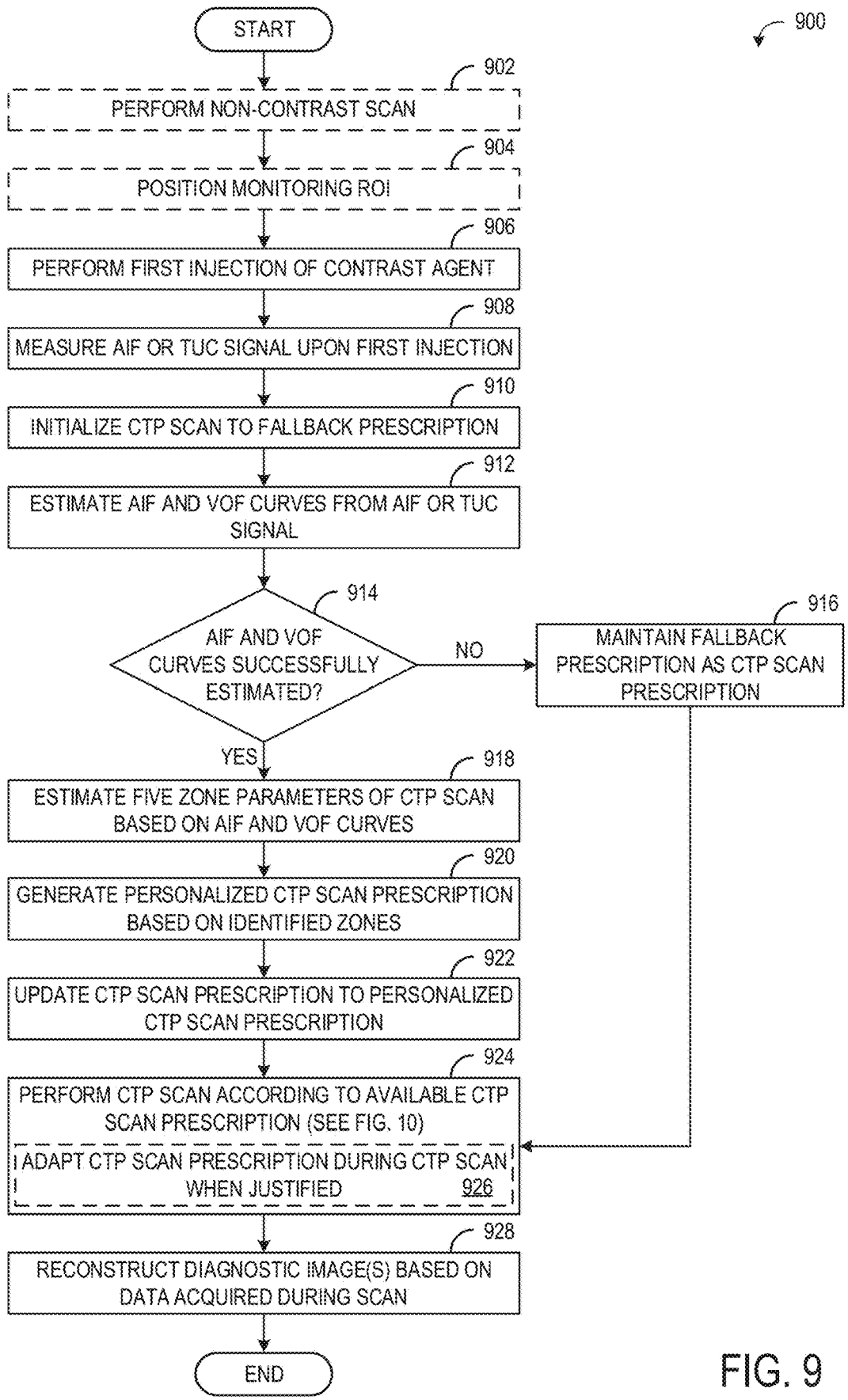
FIG. 9 is a flow chart illustrating a method for performing a personalized, five-zone perfusion scan, according to an embodiment of the disclosure.
Figure 11A:
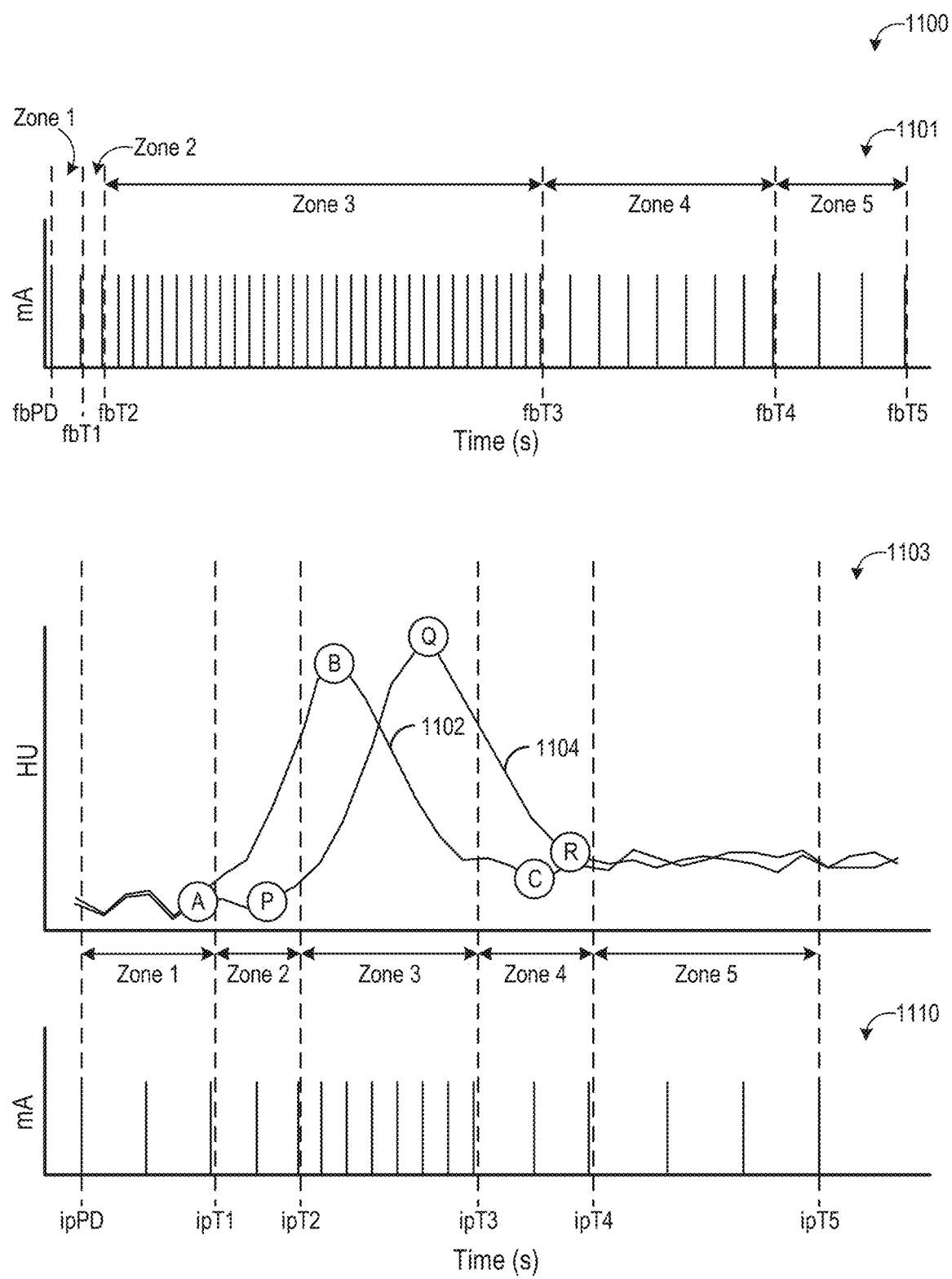
FIG. 11A is a set of graphs depicting a fallback perfusion scan prescription and a personalized perfusion scan prescription, generated based on perfusion kinetics determined for a first patient, according to the method of FIG. 9.
Figure 11B:
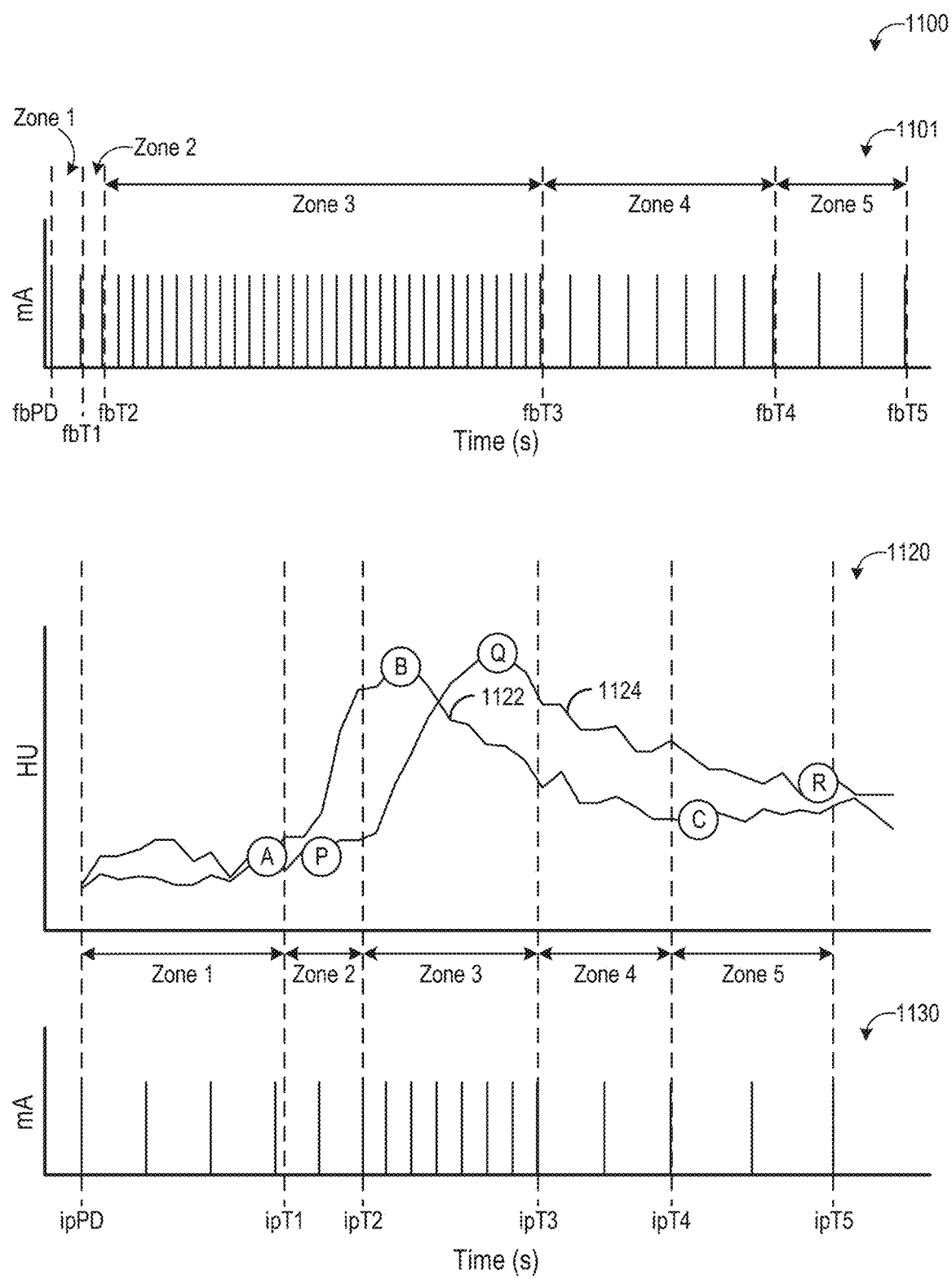
FIG. 11B is a set of graphs depicting a fallback perfusion scan prescription and a personalized perfusion scan prescription, generated based on perfusion kinetics determined for a second patient, according to the method of FIG. 9.
Figure 12:
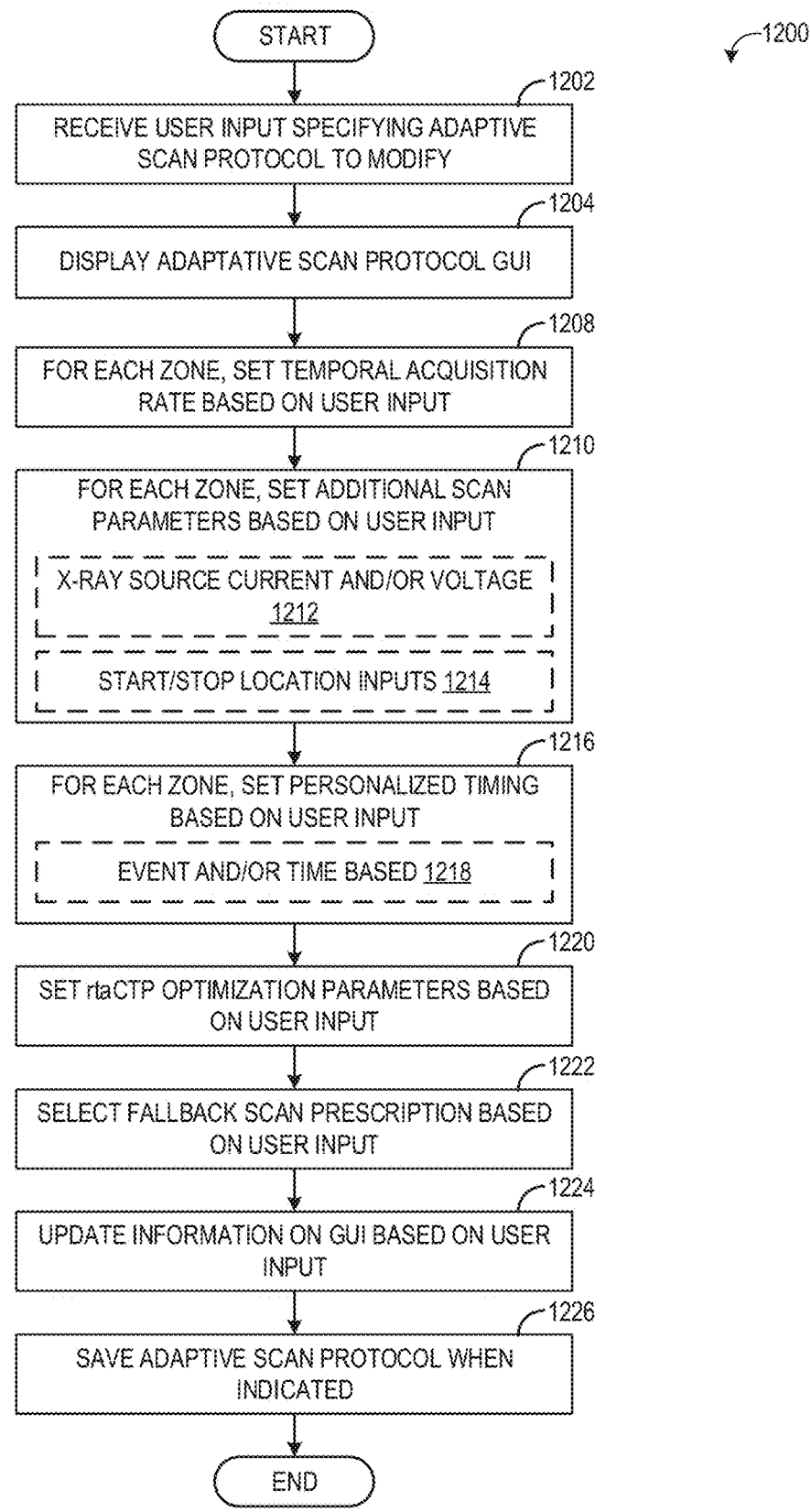
FIG. 12 is a flow chart illustrating a method for setting adaptive contrast scan settings in advance via an adaptive scan protocol graphical user interface (GUI), according to an embodiment of the disclosure.

A method for adaptive scan control, such as the method shown in FIG. 9, may include measuring the AIF or TUC signal for a patient from a first contrast bolus, determining the timing of a plurality of zone transitions for a CTP scan from the AIF or TUC signal via a model, and carrying out the CTP with a scan prescription that is determined based on the plurality of zone transitions. Further, the scan prescription may be further updated based on contrast agent kinetics measured during a first portion of the CTP scan, such as according to the method shown in FIG. 10. Such methods enable personalization of when certain changes to scan parameters (e.g., frame rate) are executed. FIGS. 11A and 11B show example scan prescriptions adaptations for different patients relative to a same fallback prescription. Further, one or more contrast scan protocols may be defined in advance via an adaptive contrast scan GUI, such as according to the method shown in FIG. 12. Example adaptive scan protocol GUIs that may be displayed during the execution of the method of FIG. 12 are shown in FIGS.

Figure 16:
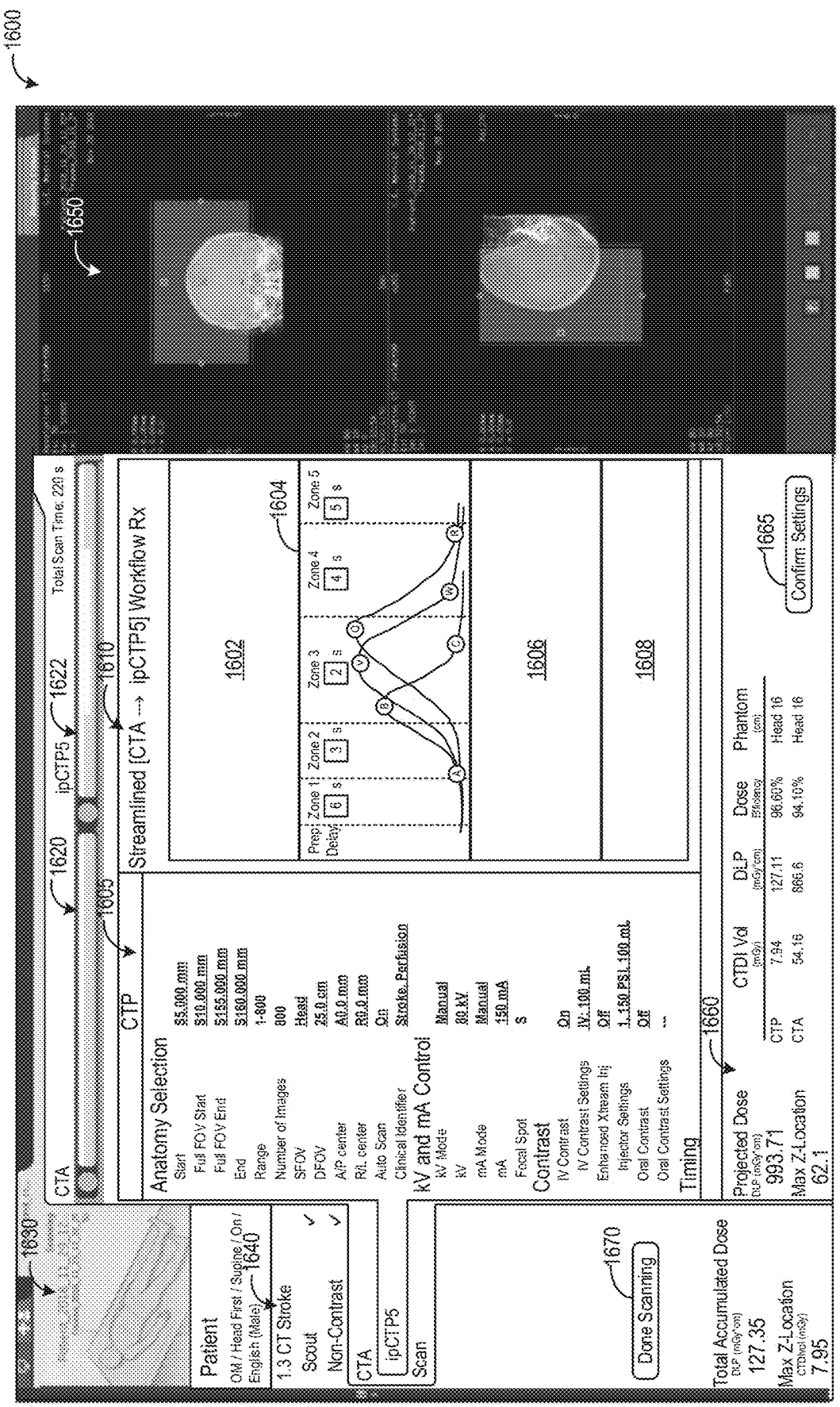
FIG. 16 shows an example of an adaptive scan run-time GUI, according to an embodiment of the disclosure.

13-15. An example run-time GUI that may be displayed during the execution of the method of FIG. 9, for example, is shown in FIG. 16.

Though a CT system is described by way of example, it should be understood that the present techniques may also be useful when applied to images acquired using other imaging modalities, such as tomosynthesis, MRI, C-arm angiography, and so forth. The present discussion of a CT imaging modality is provided merely as an example of one suitable imaging modality. Further, while the present techniques may be discussed herein with respect to head/neck scans such as acute stroke scan protocols, the present techniques may be applied during other contrast scan protocols, such as cardiac scans.

FIG. 1 illustrates an exemplary CT system 100 configured for CT imaging. Particularly, the CT system 100 is configured to image a subject 112, such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray source 104 configured to project a beam of x-ray radiation 106 for use in imaging the subject 112. Specifically, the x-ray source 104 is configured to project the x-rays 106 towards a detector array 108 positioned on the opposite side of the gantry 102. Although FIG. 1 depicts only a single x-ray source 104, in certain embodiments, multiple x-ray radiation sources and detectors may be employed to project a plurality of x-rays 106 for acquiring projection data at different energy levels corresponding to the patient. In some embodiments, the x-ray source 104 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray tube-detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some CT imaging system configurations, a radiation source projects a cone-shaped beam which is collimated to lie within an X-Y-Z plane of a Cartesian coordinate system and generally referred to as an "imaging plane." The radiation beam passes through an object being imaged, such as the patient or subject 112. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detector elements are acquired separately to produce a transmission profile.

In some CT systems, the radiation source and the detector array are rotated with a gantry within the imaging plane and around the object to be imaged such that an angle at which the radiation beam intersects the object constantly changes. A group of radiation attenuation measurements, e.g., projection data, from the detector array at one gantry angle is referred to as a "view." A "scan" of the object includes a set of views made at different gantry angles, or view angles, during one revolution of the radiation source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, a positron emission tomography (PET), or a single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to in the art as the filtered back projection technique. Transmission and emission tomography reconstruction techniques also include statistical iterative methods, such as maximum likelihood expectation maximization (MLEM) and ordered-subsets expectation-reconstruction techniques, as well as iterative reconstruction techniques. This process converts the attenuation measurements from a scan into integers called "CT numbers" or "Hounsfield units" (HU), which are used to control the brightness of a corresponding pixel on a display device.

To reduce the total scan time, a "helical" scan may be performed. To perform a "helical" scan, the patient is moved while the data for the prescribed number of slices are acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image are generated but a viewable image is not. Therefore, as used herein, the term "image" broadly refers to both viewable images and data representing a viewable image. However, many embodiments generate (or are configured to generate) at least one viewable image.

FIG. 2 illustrates an exemplary imaging system 200 similar to the CT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the x-ray beams 106 (see FIG. 1) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician may consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which, in turn, may control a table 228 which may be a motorized table. Specifically, the table motor controller 226 may move the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200, and instead, the computing device 216 may perform one or more functions of the image reconstructor 230. Moreover, the image reconstructor 230 may be located locally or remotely and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

The various methods and processes (such as the method described below with reference to FIG. 9) described further herein may be stored as executable instructions in non-transitory memory on a computing device (or controller) in the imaging system 200. In an embodiment, the computing device 216 may include the instructions in non-transitory memory, and may apply the methods described herein, at least in part, to measure the AIF or TUC signals from a plurality of reconstructed images after receiving the reconstructed images from the image reconstructor 230. The computing device 216 may use the marker in order plan personalized contrast scan prescriptions, and so forth, as described below. In other embodiments, image reconstructor 230 may include such executable instructions in non-transitory memory, and may apply the methods described herein to adaptively plan and control contrast scans. In yet another embodiment, the methods and processes described herein may be distributed across image reconstructor 230 and computing device 216.

In one embodiment, the display 232 allows the operator to evaluate the imaged anatomy, view measured and/or estimated AIF and VOF curves, trigger aspects of the contrast scans, and the like. The display 232 may also allow the operator to select a region of interest (ROI) and/or request patient information, for example, via a graphical user interface (GUI) for a subsequent scan or processing.

FIG. 3 shows a graph 300 depicting an example AIF curve 302 and an example VOF curve 304 each plotted as HU as a function of time. The AIF curve 302 represents the change in the arterial inflow of a contrast agent over time for a patient, and the VOF curve 304 represents the change in the venous outflow of the contrast agent over time for the patient. The AIF curve 302 may be measured at an arterial ROI, such as anterior cerebral artery or internal carotid artery, and may include a measurement of signal intensity in the arterial ROI relative to a baseline intensity (e.g., in the arterial ROI prior to contrast injection). The VOF curve 304 may be measured at a venous ROI, such as the superior sagittal sinus, and may include a measurement of the signal intensity in the venous ROI relative to a baseline intensity (e.g., in the venous ROI prior to contrast injection).

The AIF curve 302 may include an arterial ascent knee at approximately point A on the curve, an arterial peak at point B on the curve, and an arterial decent knee at approximately point C on the curve. The amount of time from contrast injection until the arterial peak is reached may be the time to arterial peak, indicated as t_AP on FIG. 3. The VOF curve 304 may include a venous ascent knee at approximately point P on the curve, a venous peak at point Q on the curve, and a venous decent knee at approximately point R on the curve. The amount of time from contrast injection until the venous peak is reached may be the time to venous peak, indicated as t_VP on FIG. 3. The amount of time from contrast injection until the venous return to baseline (VRTB) is reached may be the time to VRTB, indicated as t_VRTB on FIG. 3.

The amount of time it may take to reach the points marked on the curves in FIG. 3 may vary from patient to patient, as body weight, cardiac function, and other factors may impact the contrast agent inflow and outflow rate. As will be explained in more detail below, certain contrast scan protocols, such as perfusion and angiography scans, rely on the AIF and/or VOF curves, and the timing of one or more of the points described above (e.g., the arterial peak) may be determined and used as a trigger for commencing diagnostic imaging, adjusting scan parameters, and the like. However, some scan protocols are condensed as much as possible so that diagnostic information may be learned as quickly as possible in order to facilitate patient care. For example, scan protocols carried out as part of an acute stroke assessment may be designed to be as short as possible while still collecting the needed diagnostic image information so that patient care may be administered as quickly as possible. Thus, the amount of time to completely measure both the AIF curve and the VOF curve for a patient prior to initiation of the diagnostic scan(s) may delay patient care and negatively impact patient outcomes. Further, when the imaging system includes x-rays directed to the patient (such as the CT system described above with respect to FIGS. 1-2), it may be desired to minimize patient radiation exposure. Thus, acute stroke and other contrast scan protocols may include a short measurement of the AIF curve, for example, and scan protocol adjustments may be based on this limited information and/or certain aspects of the scan protocols may be carried out with fixed timing that is not changed from patient to patient. While such protocols may be suitable for ensuring that most scans generate sufficient diagnostic information, some scans may result in images that are not suitable for diagnosing the patient condition or may lead to unnecessary radiation exposure.

Thus, prior to or during the beginning of a contrast scan, a small segment of the AIF curve may be measured and this AIF curve measurement (referred to as an AIF signal) may be used to estimate the remainder of the AIF curve as well as the VOF curve. To ensure an accurate estimation, a machine learning model may be deployed that is trained using a plurality of different AIF signals measured from different patients along with associated full AIF and VOF curves (or associated points of interest on the AIF and VOF curves, such as the points labeled on FIG. 3 and described above). The measured AIF signal may be entered into the trained and validated machine learning model, and the model may output an estimated AIF curve and estimated VOF curve, or the model may output the time to one or more significant points of the AIF and VOF curves, such as the time to arterial peak, the time to venous peak, and the time to venous return to baseline. The scan protocols may then be adapted on the fly on a patient by patient basis using the estimated AIF and VOF curves and/or estimated time points of the AIF and VOF curves.

FIG. 4 shows a graph 400 depicting an estimated AIF curve 402 and estimated VOF curve 404 each estimated according to a first estimation method, referred to as an augmented timing bolus (aTB) estimation. A timing bolus may include a small amount of contrast agent that is administered before a contrast scan is initiated. The inflow of the contrast agent of the timing bolus may be monitored and used to set parameters for the follow-on contrast scan. As shown, a first segment 406 of the AIF curve is measured as described above (e.g., in a ROI based on change in HU level relative to a baseline level). The first segment 406 may commence when the timing bolus is administered (e.g., at time t1 in FIG. 4) and end after the arterial peak (e.g., at time t2 in FIG. 4). The first segment 406 may be entered into a model to estimate the remaining portion of the estimated AIF curve 402 and all of the estimated VOF curve 404. As a result, time points A and B are measured while time points V, C', Q', and R' are estimated. In some examples, the first segment 406 may extend beyond what is shown in FIG. 4. For example, rather than terminating the measurement of the AIF curve at time t2, the measurement may extend until another suitable, later time. As the first segment is lengthened, the accuracy of the estimation of the subsequent time points may be increased, but extending the measurement period may increase the radiation dosage to the patient.

FIG. 5 shows a graph 500 depicting an estimated AIF curve 502 and estimated VOF curve 504 each estimated according to a second estimation method, referred to as an augmented smart prep (aSP) estimation. Smart prep may refer to an in-flight AIF measurement that occurs using the same contrast agent bolus that is administered for the contrast scan. The inflow of the contrast agent of the contrast scan bolus may be monitored and used to set parameters for the in-flight contrast scan. As shown, a first segment 506 of the AIF curve is measured (as described above). The first segment 506 may commence when the contrast bolus is administered (e.g., at time t1 in FIG. 5) and end before the arterial peak (e.g., at time t2 in FIG. 5), while arterial contrast enhancement is still increasing. The first segment 506 may be entered into a model to estimate the remaining portion of the estimated AIF curve 502 and all of the estimated VOF curve 504. As a result, time point A is measured while time points B', P", C", Q", and R" are estimated. Time points P", C", Q", and R" are given a double prime notation to indicate that the estimation of these time points may not be as accurate as the estimation of those time points using the aTB estimation method, given that the aSP estimation relies on less measured data than the aTB estimation.

Thus, the AIF and VOF curves (or selected time points of the AIF and VOF curves) may be estimated using a relatively short measured segment of the AIF curve that is entered into a machine learning model. The aTB estimation method, described with respect to FIG. 4, may result in a more accurate estimation of the AIF and VOF curves than the aSP estimation method, given the additional measured data that may be entered into the model. However, the aTB estimation method relies on a timing bolus or other separate contrast agent injection, and thus may be more time-consuming than the aSP estimation method.

While the aTB and aSP estimation methods were both described as being based on a single arterial ROI, it is to be understood that multiple arterial ROIs could be measured and combined (e.g., averaged) to measure the AIF curve. Further, the VOF curve could be measured for the same time period as the AIF curve (e.g., from time t1 until the respective time t2) by monitoring a venous ROI, and the measured segment of the VOF curve could be used as input to the model in addition to the measured segment of the AIF curve, which may result in a more robust estimation of the remaining portions of the AIF and VOF curves.

The arterial ROI and venous ROI described above may be positioned at any suitable location where arterial inflow and venous outflow, respectively, of contrast agent may be detectable, and the selection of where to position the arterial ROI and/or venous ROI may depend on the scan protocol (e.g., what anatomy is going to be imaged in the contrast scan). However, some anatomy, such as the brain, may present challenges for arterial or venous ROI placement, as the ability to visualize certain anatomical features may require presence of a contrast agent. Thus, to place an arterial or venous ROI in the head/brain, a separate administration of contrast agent may be needed to even place the ROI, which may make arterial or venous ROI placement in the head unpractical. Thus, the arterial ROI and/or venous ROI may typically be placed in the neck area or another adjacent anatomy, and then the patient may be moved relative to the CT imaging system (e.g., via table movement) to position the head in the proper location for the contrast scan. However, this additional table movement may prolong the duration of the scan session and/or make some adaptive scan protocols unpractical. Thus, as will be explained below, another method for estimating the AIF and VOF curves for use in adaptive scan protocols includes monitoring tissue uptake of contrast agent over an entire view/image rather than a small ROI.

FIG. 6 shows a graph 600 depicting an example AIF curve 602, an example VOF curve 604, and an example tissue uptake curve (TUC) 606 each plotted as HU as a function of time. AIF curve 602 and VOF curve 604 may be the same as AIF curve 302 and VOF curve 304 described above with respect to FIG. 3. TUC 606 may represent the change in detected contrast agent in a tissue of interest, as the contrast agent is taken up by the tissue and then depleted from the tissue. To measure the TUC, tissue of interest (e.g., the brain parenchyma) may be segmented in each of a plurality of reconstructed images, and the overall or average HU of in the segmented region of each of the plurality of reconstructed images may be determined relative to a baseline level and plotted over time. Additional details regarding the tissue segmentation and TUC signal measurement are provided below with respect to FIG. 16.

The AIF curve 602 may include the time points discussed above (e.g., A, B, and C) and the VOF curve 604 may include the time points discussed above (e.g., P, Q, and R). TUC 606 may include an ascent knee at approximately point U on the curve, a TUC peak at point V on the curve, and a decent knee at approximately point W on the curve. The timing of significant points is shown in FIG. 6, including t_AP, t_VP, and t_VRTB.

A segment of the TUC may be measured and then entered into a model to predict the AIF curve and the VOF curve, the remainder of the TUC, and/or time points of interest, similar to the aTB and aSP estimation methods described above. FIG. 7 shows a graph 700 depicting an estimated AIF curve 702, an estimated VOF curve 704, and an estimated TUC 706, each estimated according to a first TUC estimation method. The tissue uptake of a contrast agent (e.g., of a timing bolus) may be monitored and used to set parameters for the follow-on contrast scan. As shown, a first segment 708 of the TUC is measured as described above (e.g., a change in HU level relative to a baseline level measured across a plurality of images). The first segment 708 may commence when the timing bolus is administered (e.g., at time t1 in FIG. 7) and end after the TUC peak (e.g., at time t2 in FIG. 7). The first segment 708 may be entered into a model to estimate the remaining portion of the estimated TUC 706 and all of the estimated AIF curve 702 and VOF curve 704. As a result, time points U and V are measured while time points A', B', C', V, Q', and R' are estimated.

FIG. 8 shows a graph 800 depicting an estimated AIF curve 802, an estimated VOF curve 804, and an estimated TUC 806 each estimated according to a second TUC estimation method. The second TUC estimation method may be performed in-flight with a contrast scan, using the same contrast agent bolus that is administered for the contrast scan. The tissue uptake of the contrast agent may be monitored and used to set parameters for the in-flight contrast scan. As shown, a first segment 808 of the TUC curve is measured (as described above). The first segment 808 may commence when the contrast bolus is administered (e.g., at time t1 in FIG. 8) and end before the TUC peak (e.g., at time t2 in FIG. 8), while tissue uptake is still increasing. The first segment 808 may be entered into a model to estimate the remaining portion of the TUC 806 and all of the estimated AIF curve 802 and all of the estimated VOF curve 804. As a result, time point U is measured while time points A'', B'', V'', W'', P'', C'', Q'', and R'' are estimated. Time points with a double prime notation indicate that the estimation of these time points may not be as accurate as the estimation of those time points using the first TUC estimation method, given that the second TUC estimation relies on less measured data than the first TUC estimation.

Thus, the AIF, TUC, and VOF curves (or selected time points of the AIF, TUC, and VOF curves) may be estimated using a relatively short measured segment of the TUC that is entered into a machine learning model. The first TUC estimation method, described with respect to FIG. 7, may result in a more accurate estimation of the AIF and VOF curves than the second TUC estimation method described with respect to FIG. 8, given the additional measured data that may be entered into the model. However, the first TUC estimation method may rely on a timing bolus or other separate contrast agent injection, and thus may be more time-consuming than the second TUC estimation method.

In some examples, a contrast scan may include a CT perfusion scan (referred to as a CTP scan). A CTP scan may produce diagnostic images showing blood profusion and delivery of blood or blood flow to a tissue of interest, such as a brain. A first example of a typical CTP protocol of the head may include a series of acquisitions performed at a single frame rate (e.g., one acquisition each 1.8 s) for a fixed duration (e.g., 87 s) following injection of a contrast bolus (assuming a prep delay between injection of the contrast bolus and the first acquisition of 5-7 s). In second example of a typical CTP protocol of the head, the acquisitions may be carried out at two different frame rates, for example a first frame rate (e.g., of one acquisition every 2 s) for a first duration (e.g., of 31 s) and then a second frame rate (e.g., of one acquisition every 5 s) for a second duration (e.g., of 35 s, for a total of 66 s) following injection of the contrast bolus (assuming the prep delay between injection of the contrast bolus and the first acquisition of 5-7 s). Ideally, a patient would be scanned at a higher frame rate during contrast enhancement (e.g., during the arterial and venous peaks), and scanning would end soon after the contrast agent returned to baseline. In the first example CTP protocol, a majority of patients, regardless of individual AIF and VOF curves, would be scanned such that diagnostic images are obtained, but some patients may be over-scanned. For example, patients with relatively short AIF/VOF peak times may be scanned for a relatively long duration after the contrast agent has returned to baseline, resulting in overly lengthy scan times and unnecessary radiation doses. In the second example CTP protocol, some patients (e.g., those with relatively long AIF/VOF peak times, such as older patients or patients with atrial fibrillation) may be under-scanned such that sufficient images as contrast is being washed out are not obtained, resulting in image quality issues (e.g., unreliable penumbra/blood flow quantitation, which may lead to an incorrect decision being made regarding whether the patient should receive an endovascular thrombectomy or other treatment). Thus, with typical CTP protocols, a tradeoff may be made between ensuring high quality images for all patients and increased exam time and corresponding increased radiation dose for some patients.

Thus, according to embodiments disclosed herein, an idealized, personalized "five-zone" CTP scan may be carried out based on the patient-specific contrast signal and output of the machine learning model described above (e.g., based on the estimated AIF and VOF curves). The CTP scan protocol may be divided into five zones (e.g., time ranges), with each zone having specified scan parameters (e.g., frame rate, tube current, etc.). The times at which each zone transition (e.g., from one zone to the next zone) are to occur may be estimated using the machine learning model based on the measured contrast signal (e.g., measured from a prior contrast scan) as input to the machine learning model. The scan prescription for the CTP scan (e.g., the CT system parameters for carrying out the scan) may be dynamically determined prior to execution of the CTP scan based on the timing of each zone transition, such that the CTP scan may be carried out in a manner that is optimized for the specific patient. Additionally, the scan prescription may be further adjusted while the CTP scan is being performed in order to further optimize the CTP scan for the specific patient. In doing so, total scan time may be reduced, radiation exposure may be lowered, and image quality may be maintained.

Thus, FIG. 9 shows a flow chart illustrating a method 900 for carrying out a personalized five-zone CTP scan. Method 900 is described with respect to the system and components described above with respect to FIGS. 1-2 but could be carried out with other systems/components without departing from the scope of this disclosure. Method 900 may be carried out according to instructions stored in non-transitory memory of a computing device (e.g., computing device 216 of FIG. 2). Method 900 may include identification of estimated times of the transitions between five zones of a CTP scan, which may be used to determine a personalized scan prescription for carrying out the CTP scan. Thus, method 900 may be performed in response to user selection of a scanning protocol that includes a CTP, such as a stand-alone CTP, a CTA followed by a CTP, a CTP followed by a CTA, a combined CTP and CTA, etc.

At 902, a non-contrast scan is optionally performed. The non-contrast scan may be taken to establish a baseline image for the area to be monitored before delivery of a contrast agent. The baseline image may then be used to align the patient and the region of interest within the imaging device.

At 904, a monitoring region of interest (ROI) for contrast monitoring is optionally identified/positioned. The monitoring ROI may comprise a specific region of the patient wherein contrast level is monitored during the scan. In some examples, the monitoring ROI may be positioned outside of the area of the patient to be imaged. In other examples, the monitoring ROI may be positioned within the imaging area such that the projection data acquired for diagnostic purposes may also be used for monitoring. Thus, an operator may select the monitoring ROI based on the baseline image acquired at 902. Determining the monitoring ROI may therefore comprise receiving a selection of a monitoring ROI from an operator, for example via operator console 220 of FIG. 2. In some examples, a monitoring ROI may be not be identified/positioned. Rather, the monitoring ROI may be segmented tissue from a plurality of reconstructed images (e.g., when the tissue uptake curve signal is used to estimate the AIF/VOF curves and/or time points of interest).

At 906, a first injection of contrast agent into the patient is performed. As a non-limiting example, the contrast agent may comprise iodine. As other examples, the contrast agent may comprise an ionic contrast medium such as meglucamine diatriozoate, or a non-ionic contrast medium such as iopromide or ohexol. The contrast agent may be intravenously injected using either automatic or manual methods. The first injection may be a timing bolus, or the first injection may be a contrast bolus for an in-flight contrast scan other than the CTP, such as a CTA performed before the CTP or a prior CTP.

At 908, an AIF or TUC signal is measured at the monitoring ROI or segmented tissue upon the first injection. As explained above with respect to FIGS. 3-6, the AIF signal may include a first portion of an AIF curve that is measured at an arterial ROI. Depending on the scanning protocol, the AIF segment may include and extend past the arterial peak (when the first contrast agent injection is a timing bolus), as shown in FIG. 4, or the AIF segment may not include the arterial peak (when the first contrast agent injection is the contrast agent injection for the first contrast scan), as shown in FIG. 5. Likewise, depending on the scanning protocol, the TUC segment may include and extend past the tissue uptake peak (when the first contrast agent injection is a timing bolus), as shown in FIG. 7, or the TUC segment may not include the tissue uptake peak (when the first contrast agent injection is the contrast agent injection for the first contrast scan), as shown in FIG. 8. To measure the AIF signal or the TUC signal, a plurality of images of the monitoring ROI may be reconstructed (e.g., by image reconstructor 230 of FIG. 2) from projection data obtained by the CT system (e.g., from projection data obtained via detector array 108, which detects x-rays generated by x-ray source 104) with a relatively low x-ray dose (e.g., a tube current of 100 mAs or less). When the AIF signal is obtained, the monitoring ROI may be an artery, and when the TUC signal is obtained, the monitoring ROI may be the entire brain (although the entire head region may be imaged, and the brain may be segmented from background/other tissue after image reconstruction). The signal intensity (e.g., in HU) of the monitoring ROI/segmented tissue relative to a baseline level for each image may be determined and plotted as a function of time to arrive at the AIF signal or TUC signal. In some examples, the AIF signal may be measured from raw projection data without requiring image reconstruction to measure the AIF signal.

The AIF signal or TUC signal may be measured for a period of time that is based on the scan protocol and patient-specific contrast uptake parameters. For example, when the first contrast injection is a timing bolus, the AIF signal or TUC signal may be measured for a first, longer period of time. In such examples, the AIF signal may be measured until just after the arterial peak is reached. The rate of change in contrast level (e.g., an instantaneous rate of change or the slope of the AIF curve) may be monitored to determine when the arterial peak has been reached. For example, a positive rate of change indicates that the contrast level is increasing, while a negative rate of change indicates that the contrast level is decreasing. Once a negative rate of change is indicated for at least two successive samples (e.g., scan acquisitions) following a positive rate of change indication for at least two successive samples (e.g., scan acquisitions) during measurement of the AIF signal, it may be confirmed that the arterial peak has been reached and the measurement may be terminated. Likewise, for the TUC signal, once a negative rate of change is indicated for at least two successive samples (e.g., scan acquisitions) following a positive rate of change for at least two successive samples during measurement of the TUC signal, it may be confirmed that the tissue uptake peak has been reached and the measurement may be terminated. When the first contrast injection is the contrast injection for the first contrast scan, the AIF signal or the TUC signal may be measured for a second, shorter period of time. In such examples, the AIF signal or TUC signal may be measured until a mid-point of the arterial contrast enhancement or a mid-point of the tissue contrast enhancement, respectively, such as until a specified number of measurement samples having a positive rate of change of contrast levels has been detected and/or until the first contrast scan is initiated by an operator of the imaging system.

At 910, method 900 includes initializing the CTP scan to a fallback prescription. The fallback prescription may include pre-determined CTP scan parameter settings that are configured to sufficiently scan nearly all patients. Initializing the CTP scan to the fallback prescription includes initializing six control points to fallback prescription settings. The first three control points are used in a first portion of the CTP scan and comprise a prep delay (PD), a time point T1 for transitioning from a first zone (e.g., zone 1) of the CTP scan to a second zone (e.g., zone 2) of the CTP scan, and a time point T2 for transitioning from the second zone to a third zone (e.g., zone 3) of the CTP scan. The final three control points are used in a second portion of the CTP scan and comprise a time point T3 for transitioning from the third zone to a fourth zone of the CTP scan, a time point T4 for transitioning from the fourth zone to a fifth zone (zone 5) of the CTP scan, and a time point T5 for ending in the fifth zone. As one example, the prep delay may define a pre-determined delay after the first injection of contrast agent has commenced, and the first zone may begin after the prep delay.

The third zone may include a highest temporal sampling rate, as will be described below. Therefore, it is desirable to capture peak contrast enhancement (e.g., the arterial and venous peaks) within the third zone. As such, the fallback prescription settings may include initializing the first three control points (PD, T1, and T2) to relatively early times and initializing the final three control points (T3, T4, and T5) to relatively late times in order to extend the third zone. By initializing the first three control points to relatively early times, patients having early peaking AIF curves may be accommodated, and by initializing the final three control points to relatively late times, patients having late venous returns to baseline times may also be accommodated.

The fallback prescription may further include settings for a temporal sampling rate of each zone. The temporal sampling rate may also be referred to as a temporal acquisition rate or frame rate and may include the frequency at which imaging system acquisitions (also referred to as passes) are performed. For example, the temporal sampling rate may be highest in zone 3 (e.g., every 2 seconds) and lowest in zones 1 and 5 (e.g., every 5 seconds). As another example, the fallback prescription may include, for most of the scan prescription, a highest temporal sampling rate indicated for any aspect of the CTP scan (e.g., the temporal sampling rate indicated for the contrast enhancement segment). The temporal sampling rate also affects a number of exposures acquired during each zone, which may vary from zone to zone. As used herein, a scan acquisition or pass may refer to a full gantry rotation (e.g., when the brain is being imaged) or a partial gantry rotation (e.g., when the heart is being imaged). In either case, an acquisition or pass may include rotating the gantry to obtain the desired views for the anatomy/scanning protocol.

The fallback prescription scan parameters may further include a pre-defined x-ray source current and a predefined x-ray source voltage. The pre-defined x-ray source current and the pre-defined x-ray source voltage may be the same or different for each zone of the CTP scan. Note that other parameter settings may also be included in the fallback prescription without parting from the scope of this disclosure.

At 912, the AIF and VOF curves may be estimated based on the AIF or TUC signal. As explained above, the AIF or TUC signal may include a measured segment of the AIF curve or the TUC that may be used as input to a model, and the model may output the estimated AIF curve and the estimated VOF curve. The model may be a suitable machine learning model, such as a decision tree, regression model, neural network, and so forth. The regression model may include a bootstrap algorithm that is trained with a dataset of N samples, where each sample includes a measured signal (whether entire AIF and VOF curves, or select features such as rate of change at the ascent of the AIF curve, AIF peak time and height, and/or AIF knee time and height) from a respective patient and identified (e.g., by an expert) ground truth, such as HU and time values for certain points of interest on the AIV and/or VOF curves (e.g., A, B, C, Q, R), such that a plurality of measured signals and corresponding ground truths from a plurality of different patients are included in the dataset. The bootstrap algorithm creates random sub-samples of the dataset with replacement to output multiple values of a desired statistic, such as a mean. The average of those multiple values provides a robust estimate of the statistic. For example, the bootstrap algorithm may be applied to determine multiple values of each of a mean time to arterial peak, a mean time to venous peak, and a mean time to venous return to baseline, with each mean value correlated to an input measured signal. In some examples, the bootstrap algorithm may be aggregated where predictions (e.g., of the means described above) from multiple decision trees may be combined to reduce variance and overfitting. Cross-validation may be performed, where the input data (e.g., training dataset) is divided into n subsets, the regression model is trained with n−1 subsets, and the remaining subset is used to test the model to avoid overfitting.

In another example, the model may be a neural network that includes artificial neurons (referred to as units or nodes) arranged in a series of layers. The input units of the neural network receive information (e.g., the AIF or TUC signal), hidden units of the network process the information, the processed information is connected on positive or negative weights, and output units of the network signal a response to the learned information. In some examples, prior knowledge is used to reduce variance and improve generalizations and training data is run through the network and used to continuously change the weight vector of the network in response to a cost function, which improves the probability of an accurate output. In other words, the neural network may comprise a plurality of nodes/layers, including an input layer that receives the AIF or TUC signal and an output layer that outputs an estimated AIF curve and an estimated VOF curve (or estimated time to arterial peak, time to venous peak, and time to venous return to baseline), with connections/weights of the layers/nodes determined based on a training dataset. The training dataset may include a plurality of pairs of data, with each pair of data including measured AIF and VOF curves and an associated AIF or TUC signal, or with each pair of data including an AIF or TUC signal and corresponding time points of interest for a plurality of patients (e.g., t_AP, t_VP, and t_VRTB).

At 914, it is determined if the AIF and the VOF curves have been successfully estimated. In some examples, the model may not be able to successfully output the AIF and VOF curves, and thus, the five zone parameters may not be determined. For example, the computing device may be unable to determine the AIF and the VOF curves using the model described above when the input AIF or TUC signal is "spikey" (e.g., includes sharp increases followed by sharp decreases) or has a high noise level. The computing device may perform one or both of a derivative and a continuity analysis of the AIF or TUC signal to evaluate a quality of the signal to determine if the AIF and the VOF curves may be successfully estimated, at least in some examples. As another example, additionally or alternatively, the computing device may perform a plausibility check on the estimated AIF and VOF curves. For example, a distance between the arterial knee and the arterial peak is expected to be proportional to a distance between the arterial peak and the arterial washout. As such, the plausibility check may compare the distance between the arterial knee and the arterial peak to the distance between the arterial peak and the arterial washout for an expected proportionality. In other examples, because the estimations may be made from very truncated information, such as when the aSP method is used to estimate the AIF and VOF curves, the system may perform a confidence assessment of the five zone parameters. In particular, the confidence assessment may be weighted toward the determined control points of the first portion of the CTP scan (e.g., PD, T1 and T2).

If the AIF and VOF curves have not been successfully estimated, method 900 proceeds to 916 and includes maintaining the fallback prescription as the CTP scan prescription. Because the system is already initialized to the fallback prescription, the control points defining each zone, the acquisition rates for each zone, and the x-ray source current voltage for each zone will not be adjusted. As such, the CTP scan prescription will not be personalized to the patient's hemodynamics (e.g., blood flow kinetics), but will ensure that the CTP scan results in diagnostically relevant information.

If the AIF and VOF curves have been successfully estimated, method 900 proceeds to 918, and the five zones of the CTP scan may then be estimated base on the estimated AIF and VOF curves and/or the estimated time points of interest. As one example, the first zone may be set to begin when the first injection of contrast agent begins, or the first zone may begin after a predefined delay after the first injection has commenced (e.g., the prep delay). A first transition from the first zone to the second zone may be identified based on the timing of the arterial ascent knee, and the time point T1 may be set accordingly. For example, the first transition from the first zone to the second zone may be estimated to occur two seconds before the arterial ascent knee (e.g., two seconds before time point A). A second transition from the second zone to the third zone may be identified based on the arterial peak (point B), and the time point T2 may be set accordingly. For example, the second transition may be estimated to occur two seconds before the arterial peak. A third transition from the third zone to the fourth zone may be identified based on the venous peak (point Q), and the time point T3 may be set accordingly. For example, the third transition may be estimated to occur two seconds after the venous peak. A fourth transition from the fourth zone to the fifth zone may be identified based on the venous return to baseline (VRTB, point R), and the time point T4 may be set accordingly. For example, the fourth transition may be estimated to occur two seconds after the VRTB. The fifth zone may end at a fixed time after the VRTB, such as fourteen seconds after VRTB, and the time point T5 may be set accordingly.

At 920, a personalized CTP scan prescription is generated based on the identified zones/zone transitions (e.g., control point settings). For example, as explained above, values for one or more scan parameters may be adjusted for one or more zones, such as the control point timing, the frame rate, the tube current, the tube voltage, etc., and thus, the personalized CTP scan prescription may include instructions for when to adjust the values of the scan parameters. As an example, generating the scan prescription may include adjusting the frame rate of the CT system at one or more zone transitions. In this way, some zones (e.g., the third zone) may have a higher frame rate than other zones (e.g., the fifth zone), and the transition from a lower frame rate to a higher frame rate or vice versa may be made when a selected zone transition is estimated to occur.

At 922, method 900 includes updating the CTP scan prescription to the personalized CTP scan prescription. Because the five zone parameters have been successfully estimated and the personalized CTP scan prescription generated accordingly, the fallback prescription need not be performed. Thus, the scan parameter settings may be updated from the fallback prescription parameter settings to include the parameter settings of the personalized CTP scan prescription.

At 920, the CTP scan is performed according to the available CTP scan prescription. The available CTP scan prescription may be the fallback prescription (e.g., when the five zone parameters have not been successfully estimated) or the personalized CTP scan prescription generated at 920 (e.g., when the five zone parameters have been successfully estimated). Carrying out the CTP scan according the available scan prescription will be described below with respect to FIG. 10. Further, as will be explained below, performing the CTP scan optionally includes adapting the CTP scan prescription during the CTP scan when justified, as indicated at 926. Briefly, settings for the second portion of the CTP scan (e.g., the final three control points) may be further refined based on data obtained during the first portion of the CTP scan resulting in a CTP scan that is further optimized for the specific patient.

At 928, one or more diagnostic images are reconstructed based on data acquired during the CTP scan. For example, one or more diagnostic images may be reconstructed using known reconstruction techniques, such as filtered back projection or iterative reconstruction. When two contrast scans are carried out, images may be constructed for each scan, e.g., CTA images and CTP images. The one or more diagnostic images may be output to a display device (e.g., display device 232 of FIG. 2) for display to an operator or a physician, to a storage medium (e.g., mass storage 218 of FIG. 2) for retrieving at a later time, and so on. Method 900 may then end.

Method 900 described above may be applied in various scan protocols, such as when a CTP is performed following a timing bolus or when a CTA or mCTA is performed first followed by the CTP. In examples where the CTP is performed after a CTA, the scan prescription for the CTP may be generated based on contrast enhancement measured upon contrast agent injection for the CTA or multi-phase CTA (mCTA) scan. When a CTA is performed before the CTP, additional measurements of the AIF or TUC signal may be obtained between CTA acquisitions, and all of the CTA information (e.g., the AIF or TUC signal and the information from the mCTA itself) may be used as input to better estimate the remainder of the AIF and the VOF (assuming the VOF was not captured) to establish the optimal timing transition (and acquisition end) timings for personalized five zone CTP prescription.

Further, while the AIF signal may include a direct measurement of time point A (the arterial ascent knee), the time when A occurs in the monitoring ROI for the CTA scan (for example, the aortic arch) may be different than when A occurs in the head (e.g., at the circle of Willis) where the CTP acquisitions will actually occur. This difference may be accounted for by adjusting the estimated AIF and VOF curves and/or time points of interest or by adjusting the AIF signal that is entered to the model.

When method 900 is performed, the scan protocol may result in a streamlined workflow that automatically computes the scan prescription for the CTP scan before the start of the second contrast bolus (for the CTP). In some examples, this may include a fully automated workflow where the system automatically computes and updates the CTP scan prescription, and then actuates the contrast injection to start at the target time (e.g., at the estimated VRTB for the first contrast injection) and proceeds to perform the personalized, five zone CTP scan. In other examples, the workflow may be semi-automatic, where the system suggests an update of the CTP scan prescription to the user relative to a fallback, fixed CTP protocol and the user has the opportunity to select or reject the updated CTP scan prescription.

Additionally, when the acquisitions are complete and as projection data is sent for image reconstruction/post-processing, the actual AIF/VOF curves may be generated as a first step to the perfusion map computation. In some examples, a post-scan workflow may include displaying to the user a comparison of the AIF/VOF estimates used to generate the CTP scan prescription vs the actual measured AIF and VOF curves. The differences between the estimated and measured AIF/VOF curves may be used to inform the user of the accuracy of the AIF/VOF estimates, inform the user of any errors in the estimates that might have impacted diagnostic image quality, and/or update the machine learning estimation models.

Figure 10:
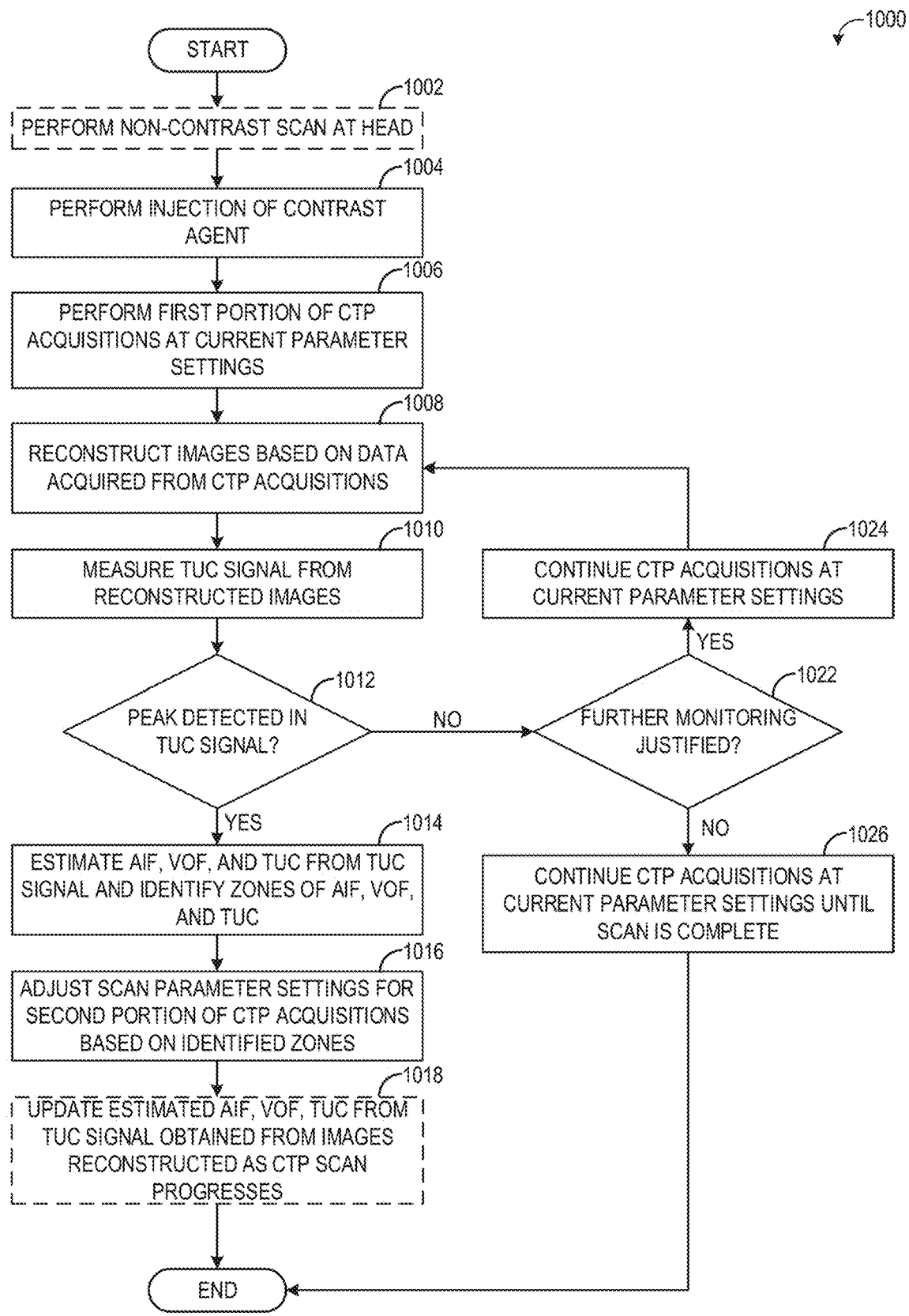
FIG. 10 is a flow chart illustrating a method for performing an adaptive perfusion scan, according to an embodiment of the disclosure.

Continuing to FIG. 10, a flow chart illustrating a method 1000 for carrying out a personalized adaptive CTP scan is shown. Method 1000 is described with respect to the system and components described above with respect to FIGS. 1-2 but could be carried out with other systems/components without departing from the scope of this disclosure. Method 1000 may be carried out according to instructions stored in non-transitory memory of a computing device (e.g., computing device 216 of FIG. 2). Method 1000 may include updating a scan prescription for carrying out the CTP scan while the CTP scan is in progress. In some examples, method 1000 may be performed as a part of another contrast scan method, such as method 900 of FIG. 9 (e.g., at 924). In other examples, method 1000 may be performed independently in response to user selection of a scanning protocol that includes a CTP, such as a stand-alone CTP, a CTA followed by a CTP, a CTP followed by a CTA, a combined CTP and CTA, etc.

At 1002, a non-contrast scan is optionally performed. As described above at 902 of FIG. 9, the non-contrast scan may be taken to establish a baseline image for the area to be monitored before delivery of a contrast agent. The non-contrast scan may be of the head in the example method presented herein, but it is to be understood that the non-contrast scan may be performed at another suitable anatomical region depending on the scan protocol.

At 1004, an injection of contrast agent into the patient is performed. For example, the injection may be a second injection performed after (e.g., later in time) than the first injection at 906 of FIG. 9. As a non-limiting example, the contrast agent may comprise iodine. In other examples, the contrast agent may comprise an ionic contrast medium such as meglucamine diatriozoate, or a non-ionic contrast medium such as iopromide or ohexol. The contrast agent may be intravenously injected using either automatic or manual methods. The injection may be a contrast bolus for an in-flight CTP scan and may be the only contrast injection performed for the CTP scan, while other injection(s) may be performed for other contrast scans performed in series with the CTP scan, for example.

At 1006, a first portion of CTP acquisitions are performed at current scan parameter settings. The current scan parameter settings may be dictated by a currently available CTP scan prescription. The currently available CTP scan prescription may be a personalized CTP scan prescription generated based on five zone parameters estimated during a prior contrast scan acquisition (e.g., a CTA scan), such as described above at 920 of FIG. 9, or may be a fallback prescription, such as described above with respect to 910 of FIG. 9. The current scan parameter settings may include, for example, temporal resolution settings for each zone of the CTP scan, control point timings for each zone of the CTP scan, and x-ray source current and voltage settings for each zone of the CTP scan, as elaborated above with respect to FIG. 9. Further, the first portion of the CTP acquisitions may refer to acquisitions performed in the first three zones (e.g., up until time point T3 for transitioning from the third zone to the fourth zone).

At 1008, one or more images are reconstructed from the data acquired during the CTP acquisitions. In some examples, the images may be "coarse" images may be reconstructed using a coarse reconstruction process that has a low computational load and thus may be performed rapidly as the CTP scan progresses. Because the images reconstructed at 1008 are not diagnostic images but instead are images reconstructed to monitor the tissue uptake of the contrast agent, the coarse reconstruction process may sacrifice diagnostic quality in order to allow the images to be quickly reconstructed. The coarse reconstruction process may include 128×128 slices that are 5 mm thick, and the reconstruction process may take about 1 second per acquisition. In other examples, any image processing that enables sufficient TUC extraction from the data acquired during the CTP acquisitions may be used.

At 1010, the TUC signal is measured from the reconstructed images. Measuring the TUC signal may include segmenting, in each coarse image, a tissue of interest, such as the brain. The segmentation process may include thresholding the image, performing an erosion process on the thresholded image, identifying the largest object, and then performing a dilation process. However, other segmentation processes may be carried out without departing from the scope of this disclosure. Once the tissue of interest has been segmented, the overall or average signal intensity (e.g., pixel brightness) for the segmented region may be determined and compared to a baseline intensity (e.g., of that tissue/segmented region prior to contrast injection). The signal intensity of each coarse, segmented image may be determined and plotted as a function of a time the image was acquired.

At 1012, method 1000 includes determining if a peak in the TUC signal has been detected. For example, a peak detector may be executed that is configured to directly detect a peak in the TUC signal and evaluate whether the detected peak is the TUC peak (e.g., time point V on FIG. 6) by determining if the detected peak meets one or more rules that define the TUC peak. The peak detector may, for each CTP acquisition, look for a peak that has a double confirm (e.g., the peak may be double confirmed when two successive CTP acquisitions are performed, each having a lower measured HU than the detected peak). If a confirmed peak is found, the found peak is considered as an internal peak candidate (IPC). If the IPC occurs before a first threshold time since the contrast injection (e.g., 14 seconds), the IPC may be discarded and the process may be repeated on the next IPC. If the IPC does not occur before the first threshold time, the IPC is further analyzed to determine if the slope of the IPC is greater than a threshold slope, such as 3 HU/s. If so, that IPC is considered a spike and is discarded. If not, the time between an ascent knee (e.g., time point U on FIG. 6) and the IPC is determined. If this time is less than a second threshold time, such as 4 seconds, the IPC is considered a spike and discarded. If not, it is determined if the median HU before the IPC is greater than a threshold value, such as the IPC HU minus 2. If so, the IPC is discarded. If not, the segmented tissue (e.g., brain) volume of the image acquisition at the IPC is compared to the segmented tissue volume from the previous image acquisition. If the segmented tissue volume at the IPC is different from the previous tissue volume by an amount that is greater than a threshold (e.g., 4.25%), the IPC is discarded. If not, (and if none of these described conditions are triggered), the IPC is confirmed as the tissue peak.

If a plausible TUC peak is detected in the TUC signal, method 1000 proceeds to 1014 to estimate an AIF curve, a VOF curve, and/or the remainder of the TUC from the TUC signal (and/or estimate the time for the arterial peak time, the venous peak time, the venous return to baseline time, and/or other time points of interest). The AIF curve, the VOF curve, and/or the remainder of the TUC may be estimated from the TUC signal by inputting the TUC signal into a machine learning model. As explained above, the TUC signal may include a measured segment of the TUC that may be used as input to a model, and the model may output the estimated AIF curve, the estimated VOF curve, and/or the remainder of the TUC. The model may be a suitable machine learning model, such as a decision tree, regression model, neural network, and so forth. The regression model may include a bootstrap algorithm that is trained with a dataset of N samples, where each sample includes a measured signal (whether entire AIF and VOF curves and/or TUC, or select features such as the inflection points on each curve, rate of change of various segments of the curves, curve peak times and heights, and/or curve knee times and heights) from a respective patient and identified (e.g., by an expert) ground truth, such as HU and time values for certain points of interest on the AIV, VOF, and TUC curves (e.g., A, B, C, Q, R, U, V, W), such that a plurality of measured signals and corresponding ground truths from a plurality of different patients are included in the dataset. The bootstrap algorithm creates random sub-samples of the dataset with replacement to output multiple values of a desired statistic, such as a mean. The average of those multiple values provides a robust estimate of the statistic. For example, the bootstrap algorithm may be applied to determine multiple values of each of a mean time to arterial peak, a mean time to venous peak, and a mean time to venous return to baseline, with each mean value correlated to an input measured signal. In some examples, the bootstrap algorithm may be aggregated where predictions (e.g., of the means described above) from multiple decision trees may be combined to reduce variance and overfitting. Cross-validation may be performed, where the input data (e.g., training dataset) is divided into n subsets, the regression model is trained with n−1 subsets, and the remaining subset is used to test the model to avoid overfitting.

In another example, the model may be a neural network that includes artificial neurons (referred to as units or nodes) arranged in a series of layers. The input units of the neural network receive information (e.g., the TUC signal), hidden units of the network process the information, the processed information is connected on positive or negative weights, and output units of the network signal a response to the learned information. In some examples, prior knowledge is used to reduce variance and improve generalizations and training data is run through the network and used to continuously change the weight vector of the network in response to a cost function, which improves the probability of an accurate output. In other words, the neural network may comprise a plurality of nodes/layers, including an input layer that receives the TUC signal and an output layer that outputs an estimated AIF curve, an estimated VOF curve, and/or estimated TUC (or estimated time to arterial peak, time to venous peak, time to venous return to baseline, and/or other time points), with connections/weights of the layers/nodes determined based on a training dataset. The training dataset may include a plurality of pairs of data, with each pair of data including measured contrast enhancement curves (e.g., AIF, VOF, TUC) and an associated TUC signal, or with each pair of data including a TUC signal and corresponding time points of interest for a plurality of patients (e.g., t_AP, t_VP, t_VRTB, etc.).

One or more zones of the CTP scan may then be identified base on the estimated AIF and VOF curves and/or the estimated time points of interest. As one example, the first zone may begin when the first injection of contrast agent begins or the first zone may begin after a predefined delay after the first injection has commenced (e.g., the prep delay). A first transition from the first zone to the second zone may be identified based on the timing of the arterial ascent knee. For example, the first transition from the first zone to the second zone may be estimated to occur two seconds before the arterial ascent knee (e.g., two seconds before time point A). A second transition from the second zone to the third zone may be identified based on the arterial peak (point B). For example, the second transition may be estimated to occur two seconds before the arterial peak. A third transition from the third zone to the fourth zone may be identified based on the venous peak (point Q). For example, the third transition may be estimated to occur two seconds after the venous peak. A fourth transition from the fourth zone to the fifth zone may be identified based on the venous return to baseline (VRTB, point R). For example, the fourth transition may be estimated to occur two seconds after the VRTB. The fifth zone may end at a fixed time after the VRTB, such as fourteen seconds after VRTB. Although five zones are described herein, the personalized CTP scan may include more or fewer than five zones without departing from the scope of this disclosure.

In examples where the ML model outputs the estimated curves, the time points discussed herein (e.g., the venous peak and the VRTB) may be determined from the estimated curves. For example, the VRTB may be identified as the point on the VOF curve where the contrast level drops back below a threshold, or where the VOF curve slope switches from a negative rate of change to no change. The venous may be identified as the point of the VOF curve where the contrast level no longer increases (e.g., for a specified number of frames, such as two) and/or as the highest contrast level of the VOF curve (e.g., a global maximum of the VOF curve).

At 1016, one or more scan parameter settings for a second portion of the CTP acquisitions are adjusted based on the identified zones/zone transitions. For example, as explained above, values for one or more scan parameters may be adjusted for one or more zones, such as temporal sampling rate, tube current, tube voltage, etc. The second portion of the CTP acquisitions may include acquisitions performed in zones 4 and 5, and thus, the data obtained from acquisitions in zones 1-3 may be used to adjust the scan parameters for zones 4 and 5. Adjusting the scan parameters may include decreasing the temporal sampling rate at each zone transition. For example, during the third zone, the temporal sampling rate may include one acquisition every 2 seconds. At the transition from the first portion of the CTP scan to the second portion of the CTP scan (e.g., from the third zone to the fourth zone at control point T3 described above), the temporal sampling rate may be decreased to one acquisition every 3-4 seconds (e.g., one acquisition every 3.5 seconds), and the system may be operated at the decreased temporal sampling rate over the course of the fourth zone. At the transition between the fourth zone and the fifth zone (e.g., at control point T4), the temporal sampling rate may again be decreased, for example to one acquisition every 5 seconds. The system may be operated at the further decreased temporal sampling rate until the end of the fifth zone. In some examples, the x-ray source current and voltage may remain constant across the entire CTP scan, regardless of the adjusted temporal sampling rates. In other examples, the x-ray source current and/or voltage may be adjusted. For example, the x-ray source current may be lowered for the second and/or third zones.

In some examples, method 1000 may include updating the estimated TUC and AIF and VOF curves using an updated TUC signal obtained from coarse images reconstructed as the CTP scan progresses, as indicated at 1018. For example, one or more images may be reconstructed from one or more of the CTP acquisitions, and the tissue segmentation and TUC signal measurement described above may be performed on these images to obtain an updated TUC signal that includes TUC data after the first portion of CTP acquisitions. This updated TUC signal may be entered into the machine learning model to provide an updated/refined estimate of the TUC and AIF and VOF curves. Method 1000 may then end.

Returning to 1012, if a plausible peak is not detected, method 1000 proceeds to 1022 to determine if further monitoring for the TUC peak is justified. As explained above, monitoring for the TUC peak includes performing fast image reconstructions in order to segment the tissue of interest and measure the contrast level signal in the segmented tissue. These fast reconstructions, while less processing intensive than the actual diagnostic image reconstructions, still use up processing resources that could otherwise be devoted to performing the diagnostic image reconstructions. Thus, the fast image reconstructions performed as part of the TUC monitoring may delay the output of the final diagnostic images. Accordingly, any reduction in the overall scan time provided by the adaptive scan prescription may be weighed against the delay provided by the TUC monitoring. Thus, determining if further monitoring is justified also includes determining whether including adaptive CTP is justified in order to assess if an expected value of time/dose savings by further tightening the CTP scan parameters outweighs the expected delay due to the real-time monitoring.

A majority of patients may exhibit a TUC peak by 35 seconds after contrast agent injection, and thus if a TUC peak is not detected by a threshold maximum amount of time (e.g., 46-65 seconds), it may be likely that a plausible peak will not be detected. Thus, an operator of the imaging system (or an administrator of the medical facility housing the imaging system, or another qualified personnel) may determine that continued monitoring for the TUC peak is not justified if the peak is not detected within a threshold monitoring duration, such as within 45-65 seconds or another suitable time. The determination of whether or not continued monitoring is justified may be made automatically based on the amount of elapsed time since the contrast agent was injected or the first CTP acquisition was performed relative to the threshold monitoring duration. The threshold monitoring duration may be set in advance by the operator or another clinician or administrator, as will be elaborated herein with respect to FIGS. 12 and 13. In some examples, the threshold monitoring duration may be selected by the operator (or other user) from a predefined range, such as 45-65 seconds.

In another example, additionally or alternatively, it may be determined that further monitoring is justified when the number of passes already performed is greater than or equal to a threshold number. The threshold number may be set in advance by the operator or another clinician or administrator, for example. As one example, the threshold number may be empirically determined, such as a median number of passes performed for a large number of patient scans (e.g., scans of 100 patients). Thus, when the number is passes already performed is not greater than or equal to the threshold number, the likelihood that further adaptive action would further reduce the number of passes is less than or equal to 50%. Additionally or alternatively, the threshold number may take into account a time cost of further monitoring. For example, monitoring for 45 seconds may delay a final reconstruction by 25 seconds, which is approximately how long it takes to reconstruct 3-4 diagnostic quality exposures. Therefore, further monitoring may not be justified when the adaptation may reduce the CTP scan by 1-3 passes, for example. In another example, additionally or alternatively, the determination of whether or not continued monitoring is justified may be made by the operator at the time of the CTP scan, such as via user input entered by the operator.

If it is determined at 1022 that further monitoring is justified, method 1000 proceeds to 1024 to continue performing CTP acquisitions at the current parameter settings, such as at the current temporal sampling rate setting and zone transition time points. Method 1000 proceeds to 1008 continue to reconstruct course images from the data acquired during the CTP acquisitions at the current parameter settings and continues to measure the TUC signal from the coarse images and monitor the TUC signal for a plausible peak. If further monitoring is not justified, for example if the TUC peak has not been detected after monitoring for the threshold monitoring duration, method 1000 proceeds to 1026 to continue CTP acquisitions at the current parameter settings until the CTP scan is complete. In such an example, the TUC signal monitoring is terminated, and all processing resources may be devoted to the diagnostic image reconstruction. Thus, the second portion of the CTP acquisitions may be acquired while operating with settings determined according to the personalized CTP scan prescription, when available, and without further real-time adjustments. Alternatively, when the personalized CTP scan prescription is unavailable, then the second portion of the CTP acquisitions may be acquired while operating with settings determined according to the fallback prescription. Method 1000 then ends.

Thus, the method described above with respect to FIG. 10 provides for an execution of a current CTP scan prescription, which may be a personalized CTP scan prescription or a fallback CTP scan prescription, that may be adapted on the fly based on individual patient contrast agent kinetics in order to reduce the number of CTP acquisitions and/or reduce the duration of the CTP scan where possible. The adaptation of the current scan prescription may be performed only if a peak of a contrast signal is detected within a predetermined time frame, and may only be adapted to reduce the temporal sampling rate/move the transition times for reducing the temporal sampling rate (and ending the scan) to earlier time points. The fallback scan prescription may be a "worst case" CTP prescription with a longest scan duration and most number of passes/acquisitions. By combining the methods of FIGS. 9 and 10 to initialize the CTP scan with the fallback prescription and then personalizing and/or adapting if possible, rather than starting with a scan prescription that has a slower temporal sampling rate during the initial portion of the scan and then either adapting or switching to the fallback if the TUC peak cannot be identified, a more robust CTP scan may be performed for all patients.

Thus, the adaptive CTP scan described herein may start at a first zone and may include scanning in the first zone at a first temporal sampling rate, first tube current, etc.; transitioning to a second zone at a first transition time T1 (which may be set based on estimated time points generated during a prior contrast scan or set according to a fallback prescription) and scanning in the second zone at a second temporal sampling rate, second tube current, etc.; transitioning to a third zone at a second transition time T2 (which may be set based on the estimated time points generated during the prior contrast scan or set according to the fallback prescription) and scanning in the third zone at a third temporal sampling rate, third tube current, etc.; transitioning to a fourth zone at a third transition time T3 (which may be set based on the estimated time points generated during the prior contrast scan or set according to the fallback prescription and further adjusted, if justified, based on a measured TUC signal obtained during zones 1-3) and scanning in the fourth zone at a fourth temporal sampling rate, fourth tube current, etc.; and transitioning to a fifth zone at a fourth transition time T4 (which may be set based on the estimated time points generated during the prior contrast scan or set according to the fallback prescription and further adjusted, if justified, based on the measured TUC signal obtained during zones 1-3) and scanning in the fifth zone at a fifth temporal sampling rate, fifth tube current, etc. The scanning in the fifth zone may stop after a suitable number of acquisitions have been performed and/or a set end time T5 is reached. In some examples, the temporal sampling rate in each zone is different. In other examples, one or more of the zones may have the same temporal sampling rate. In some examples, one or more of the zones may have the same tube current and/or one or more of the zones may have different tube current.

In some examples, when the acquisitions are complete and as projection data is sent for image reconstruction/post-processing, the actual AIF/VOF curves (or TUC) may be generated as a first step to the perfusion map computation. In some examples, a post-scan workflow may include displaying to the user a comparison of the AIF/VOF/TUC estimates used to generate the CTP scan prescription vs the actual measured TUC and/or AIF and VOF curves. The differences between the estimated and measured AIF/VOF/TUC may be used to inform the user of the accuracy of the AIF/VOF estimates, inform the user of any errors in the estimates that might have impacted diagnostic image quality, and/or update the machine learning estimation models.

Further, while method 1000 was described above with respect to a head CTP scan using a TUC signal to adapt the CTP scan prescription, the method may apply to other types of scans without departing from the scope of this disclosure. For example, the method may be used to adapt a liver CTP scan, a cardiac CTP scan, etc.

Next, FIGS. 11A and 11B show example timelines of five zone, personalized CTP scans carried out according to the methods of FIGS. 9 and 10. Referring first to FIG. 11A, it illustrates a timeline 1100 that includes a first plot 1101 showing initialized scanning events set according to a fallback scan prescription and a second plot 1103 showing estimated contrast levels determined from an aTB estimation method, an aSP estimation method, or a TUC estimation method and a measured contrast signal from a first patient. As such, plot 1103 includes an estimated AIF curve 1102 and an estimated VOF curve 1104, as explained above with respect to FIGS. 3-8. A third plot 1110 shows scanning events (with the x-ray tube current for each acquisition of the CT imaging system) adjusted according to the estimated AIF curve 1102 and the estimated VOF curve 1104. Each plot is a function of time, and the plots are time aligned. Dashed lines show time points of interest, herein the control points for the scanning zone transitions.

Referring first to the fallback scan prescription shown in the first plot 1101, scanning within the first zone (zone 1) is set to commence at a fallback prescription prep delay time (fbPD). In zone 1, the acquisitions may occur at a first frame rate setting, such as a frame rate of one acquisition every 5 seconds. A first transition may be set to occur at a first fallback prescription control time point (fbT1), and the acquisition frame rate setting may be increased to a second frame rate setting in the second zone, which may be higher than the first frame rate setting. A second transition may be set to occur at a second fallback prescription control time point (fbT2), and the acquisition frame rate setting may be further increased to a third frame rate setting in the third zone (e.g., relative to the second frame rate setting). In one example, the third frame rate setting may be in a range of 1.5 s-2.8 s, such as one acquisition every 2 seconds. A third transition may be set to occur at a third fallback prescription control time point (fbT3), and the acquisition frame rate setting may be decreased relative to the third frame rate setting to a fourth frame rate setting in the fourth zone. A fourth transition may be set to occur at a fourth fallback prescription control time point (fbT4), and the acquisition frame rate setting may be further decreased relative to the third frame rate setting to a fifth frame rate setting in the fifth zone. The fifth zone may be set to end at a fifth fallback prescription control time point (fbT5). Thus, the first zone is set to comprise a first time duration between fbPD and fbT1, during which the scan acquisitions are set to occur at the first frame rate setting; the second zone is set to comprise a second time duration between fbT1 and fbT2, during which the scan acquisitions are set to occur at the second frame rate setting; the third zone is set to comprise a third time duration between fbT2 and fbT3, during which the scan acquisitions are set to occur at the third frame rate setting; the fourth zone is set to comprise a fourth time duration between fbT3 and fbT4, during which the scan acquisitions are set to occur at the fourth frame rate setting; and the fifth zone is set to comprise a fifth time duration between fbT4 and fbT5 during which the scan acquisitions are set to occur at the fifth frame rate setting. Further, in some examples, tube current and/or voltage settings may change between zones, e.g., the tube current setting may be lowered for the fourth and fifth zones.

The CT imaging system may be initialized with the fallback prescription shown in the first plot 1101. If no adjustments are made to the CTP prescription, such as when a personalized CT scan prescription cannot be generated (see FIG. 9) or real-time adjustments cannot be made (see FIG. 10), the CTP scan will be performed according to the fallback prescription. In contrast, third plot 1110 shows adjustments to the CTP scan prescription that are made according to the estimated AIF curve 1102 and the estimated VOF curve 1104 in order to optimize the zone transitions according to the first patient's hemodynamics. Thus, third plot 1110 comprises an ideal personalized CTP prescription.

The first zone (zone 1) may be set to commence at an ideal personalized prep delay time point (ipPD), which may correspond to a prep delay (e.g., of 5 seconds) after contrast agent injection. In zone 1, the acquisitions may occur at the first frame rate, such as a frame rate of one acquisition every 5 seconds. The first transition may be set to occur at a first ideal personalized control time point (ipT1), which may be two seconds before point A on the AIF curve 1102. When transitioning to the second zone (zone 2) at ipT1, the acquisition frame rate setting may be increased, such that scanning occurs at a second frame rate in zone 2. In one example, the second frame rate may be one acquisition every 3 seconds. The second transition may be set to occur at a second ideal personalized control time point (ipT2), which may be two seconds before point B on the AIF curve 1102. When transitioning to the third zone (zone 3) at ipT2, the acquisition frame rate may be increased, such that scanning occurs at a third frame rate in zone 3. The third transition may be set to occur at a third ideal personalized control time point (ipT3), which may be two seconds after point Q on the VOF curve 1104, for example. When transitioning to the fourth zone (zone 4) at ipT3, the acquisition frame rate may be decreased relative to the third zone, such that scanning occurs at a fourth frame rate in zone 4. The fourth transition may be set to occur at a fourth ideal personalized control time point (ipT4), which may be two seconds after point R on the VOF curve 1104, for example. When transitioning to the fifth zone (zone 5) at ipT4, the acquisition frame rate may be decreased relative to the fourth zone, such that scanning occurs at a fifth frame rate in zone 5. In one example, the fifth frame rate may be one acquisition every 5-10 seconds. In some examples, only three acquisitions may occur in zone 5, and then the CTP scan may be set to end at a firth ideal personalized control time point (ipT5). In the example scan sequence shown in FIG. 11A, the tube current and voltage may be kept constant between zones. However, in some examples, the tube current and/or voltage may change between zones, e.g., the tube current may be lowered for the fourth and fifth zones.

The first three control points have been set later in the ideal personalized CTP scan prescription shown in the third plot 1110 relative to the fallback scan prescription shown in the first plot 1101. For example, ipPD is later in time than fbPD, ipT1 is later in time than fbT1, and ipT2 is later in time than fbT2. Further, the last three control points have been set earlier in the ideal personalized CTP scan prescription than in the fallback scan prescription. For example, ipT3 is earlier in time than fbT3, ipT4 is earlier in time than fbT4, and ipT5 is earlier in time than fbT5. As such, zone 3 in particular occurs over a shorter duration in the ideal personalized CTP scan prescription, resulting in fewer high frequency acquisitions. Additionally, the ideal personalized CTP scan prescription results in fewer overall acquisitions obtained over a shorter duration.

FIG. 11B shows example AIF/VOF curves and associated zones for five-zone CTP scans for a second example patient relative to the same fallback prescription shown in plot 1101. A second plot 1120 shows an example AIF curve 1122 and an example VOF curve 1124 for the second patient, plotted as HU as a function of time (as explained above with respect to FIG. 11A). A third plot 1130 further includes five zones determined according to the method of FIGS. 9 and 10. Each plot is a function of time, and the plots are time aligned. Dashed lines show time points of interest, herein the control points for the scanning zone transitions described above with respect to FIG. 11A.

The third plot 1130 shows the ideal personalized control time points for the second patient. Similar to the first patient shown in FIG. 11A, the first three control points have been set later in the ideal personalized CTP scan prescription shown in the third plot 1130 relative to the fallback scan prescription shown in the first plot 1101. For example, ipPD is later in time than fbPD, ipT1 is later in time than fbT1, and ipT2 is later in time than fbT2. Further, the last three control points have been set earlier in the ideal personalized CTP scan prescription than in the fallback scan prescription. For example, ipT3 is earlier in time than fbT3, ipT4 is earlier in time than fbT4, and ipT5 is earlier in time than fbT5. However, the ideal personalized control time points are different for the second patient relative to the first patient. As appreciated by comparing the second plot 1120 of FIG. 11B with the second plot 1103 of FIG. 11A, the first patient may have a faster ascent time and a faster descent time than the second patient. As an example, both ipT1 and ipT3 are set later for second patient relative to the first patient in order to better capture the later peaking hemodynamics of the second patient. As a result, the first zone and the fourth zone for the second patient may be longer than the first zone and the fourth zone, respectively, for the first patient. However, the third zone of the fallback scan prescription shown in first plot 1101 would accommodate both the earlier peaking AIF of the first patient and the later peaking VOF of the second patient.

By determining the transition times for each patient individually, the times when the frame rate of the scan acquisitions is adjusted may be specifically tailored for each patient. In doing so, the increase in frame rate for the second zone, for example, may be triggered just prior to the arterial ascent knee and the frame rate may be further increased for the third zone, just before the arterial peak. In this way, the adjustment of the acquisition frame rate (e.g., of the second and third zones) may be executed when indicated by the patient's individual physiology. In contrast, the fallback scan prescription is a fixed prescription, which may result in over-scanning of some patients (and thus higher than needed radiation exposure) but ensures that under-scanning does not occur.

Thus, method 900 and the corresponding timeline and plots shown in FIGS. 11A and 11B provides for using available contrast enhancement data (e.g., the AIF or TUC signal) from a first contrast injection and the subsequent acquisitions as input to a machine learning model to estimate the AIF and VOF curves and/or time points of interest of the AIF and VOF curves (e.g., the inflection points of the curves). Leveraging the estimates of the AIF and VOF curves and/or the time points of interest, the transition times between five zones spanning the AIF and VOF curves may be defined, and these transition times may be used to generate an ideal personalized 5 zone CTP (ipCTP5) scan prescription. The estimation of the AIF and VOF curves and/or the time points of interest may occur relatively quickly (e.g., under 10 ms) and thus, the entire ipCTP5 scan prescription may be completed before the venous curve of the first contrast injection even reaches baseline. In some examples, the ipCTP5 scan prescription may be further adapted in real-time during the CTP scan (e.g., while a first portion of the CTP scan is occurring), as described with respect to FIG. 10. While a five zone CTP scan prescription is described herein, it is to be understood that the CTP scan prescription may include more or fewer than five zones, and that transition between zones may occur at times other than the examples provided above. The personalized, adaptive CTP scan prescription may include frame rate changes that are triggered at any suitable time or times as a function of the patient's individual, estimated AIF/VOF curves (or AIF/VOF time points), including frame rate changes triggered before the estimated arterial peak, as will be elaborated below with respect to FIG. 13.

Next, FIG. 12 shows a flow chart illustrating a method 1200 for defining a contrast scan protocol. Method 1200 is described with respect to the system and components described above with respect to FIGS. 1-2 but could be carried out with other systems/components without departing from the scope of this disclosure. Method 1200 may be carried out according to instructions stored in non-transitory memory of a computing device (e.g., the computing device 216 of FIG. 2). Method 1200 may include the selection/adjustment of various parameters for one or more contrast scan protocols. Thus, method 1200 may be performed in response to authenticating an authorized personnel, such as a lead technologist, radiologist, hospital administrator, etc.

At 1202, a user input specifying an adaptive scan protocol to modify is received. In some examples, the computing device may store a plurality of default contrast scan protocols, and the user input may include a selection of one of the default contrast scan protocols. In other examples, the computing device may store one or more modified contrast scan protocols, and the user input may include a selection of one of the modified contrast scan protocols. In still further examples, the user input may include an indication that a new contrast scan protocol is to be defined. The contrast scan protocol may be a suitable contrast scan protocol, such as a CTP, a CTA followed by a CTP, a CTP followed by a CTA, a combined CTP and CTA, a CTA, or another contrast scan. The contrast scan protocol may be specific to a particular anatomy and/or a particular suspected patient condition. For example, the contrast scan protocol may be specific to a head, head/neck, abdomen, heart, etc., and/or the contrast scan protocol may be specific to acute stroke, myocardial infarction, liver dysfunction, etc. Further, additionally or alternatively, the contrast scan protocol may be specific to a type of patient, such as pediatric, adult, advanced age adult, small, medium, large, etc. The user input may be received from a suitable user input device, such as the operator console 220 of FIG. 2 (which may include a keyboard, a mouse, a touchscreen, and/or another suitable input device).

At 1204, an adaptive scan protocol graphical user interface (GUI) is displayed. The adaptive scan protocol GUI may be displayed on a display device communicatively coupled to the computing device, such as the display 232 of FIG. 2. The adaptive scan protocol GUI may include one or more sections via which various parameters for the contrast scan protocol may be set/adjusted. Further, the adaptive scan protocol GUI may include a visual representation of the acquisition timings for the scan protocol that may change as the user enters input to adjust/set the scan parameters, as will be described in more detail below.

At 1208, a temporal acquisition rate is set for each zone based on user input to the adaptive scan protocol GUI. As explained above, the scan protocol may include different scan parameters that may be adjusted as the contrast scan progresses, such as temporal acquisition rate. To facilitate these adjustments, the contrast scan protocol may be divided into zones. The adaptive scan protocol GUI may include a plurality of user interface inputs, such as user interface elements, each representing a respective zone (e.g., zones 1-5), and the user may specifically input parameters for each respective zone via the plurality of user interface elements. For example, the adaptive scan protocol GUI may include a temporal acquisition rate value for each zone, and the user may adjust the temporal acquisition rate for one or more zones via input to the temporal acquisition rate inputs, as will be elaborated below with respect to FIG. 13.

At 1210, additional scan parameters may be adjusted for each zone based on user input to the adaptive scan protocol GUI. The additional scan parameters may include x-ray source current and/or voltage, as indicated at 1212. For example, when the imaging system is a CT system as described herein or another x-ray imaging system, the output of the x-ray source may be adjustable for each zone by the user. The adaptive scan protocol GUI may include a current input for each zone, and the x-ray source current for each zone may be adjusted by the user via input to the current inputs. In some examples, the additional scan parameters may include scan start/stop locations, as indicated at 1214. In such examples, the adaptive scan protocol GUI may include start/stop location inputs for each zone, and the user may adjust the scan start/stop location for each zone, if desired. It is to be understood that the additional scan parameters discussed herein are exemplary, and other scan parameters may be adjusted without departing from the scope of this disclosure.

At 1216, a personalized timing for each zone is set based on user input to the adaptive scan protocol GUI. The timing may be event and/or time-based, as indicated at 1218. Event-based timing may include timing based on the start of the scan, contrast agent response curve events (e.g., venous peak, arterial peak, contrast agent washout, or other curve triggers), contrast agent detection, proportion between two events, proportion relative to an event, group number, etc. Time-based timing may include delays or advances relative to specified events and/or time since the start of the scan. The adaptive scan protocol GUI may include a timing input for each zone as well as an event input for each zone. The user may set or adjust when each selected zone is to end by adjusting the respective timing and event inputs. For example, the timing input may be set in order to delay or advance a zone transition (where one zone ends and the next zone begins) by a specified amount of time relative to an event defined by selection of the corresponding event input. As a non-limiting example, a first zone may be specified as ending at a given time (e.g., 2 seconds) relative to an event (e.g., venous peak of the patient's contrast level curve) by setting the time of the timing input for the first zone and setting the event input of the first zone. The determination of whether the zone ends before or after the specified event may be based on whether positive or negative time is specified in the timing input. For example, positive time may indicate the zone is to end after the specified event while negative time may specify the zone is to end before the specified event. However, in some examples, an additional input may be present on the GUI which may be adjusted to specify before or after.

As explained above, the events that may be selected to trigger zone transitions may include events of a patient contrast level curve. A patient contrast level curve may be determined for the patient at the time the contrast scan is actually executed to image the patient. The patient contrast level curve may include an AIF curve, a tissue uptake curve (TUC), and/or a VOF curve. The AIF curve may represent the change in contrast level (after a contrast agent has been administered to the patient) at an artery of the patient, the TUC may represent the change in contrast level in a segmented tissue of the patient, such as the brain, and the VOF curve may represent the change in contrast level at a vein of the patient. Each patient may have a different contrast level curve (e.g., different peak timing, different peak height, different ascent knee length/slope, different descent knee length/slop, etc.). The contrast level curve for a patient may be measured before the contrast scan. However, additional optimization to the parameters may be made based on a contrast level measured during the contrast scan via real-time adaptive CTP (rtaCTP).

Thus, at 1220, rtaCTP optimization parameters are set based on user input to the adaptive scan GUI. As will be elaborated below with respect to FIGS. 13-15, setting the rtaCTP optimization parameters may include setting when to perform real-time optimization (e.g., if justified, never, or always) as well as parameters for justifying the rtaCTP optimization. For example, the rtaCTP optimization may be justified when the number of passes is greater than or equal to a threshold number set by the user and when a scan time is less than a maximum monitoring duration set by the user.

In this way, the adaptive scan protocol GUI may allow the lead technologist or other user to specify scan parameters that change during the contrast scan (including when the scan is complete) based on patient-specific contrast agent kinetics without knowing the patient-specific contrast agent kinetics ahead of time. As such, during execution of an adaptive scan protocol (e.g., while executing method 900 of FIG. 9 and/or method 1000 of FIG. 10), the actual scan prescription that dictates the number and timing of passes/acquisitions of the imaging system (e.g., gantry rotations) and the settings for each acquisition (e.g., x-ray tube current) may be set based on the parameters defined by the scan protocol and adapted on the fly, automatically, when the imaged patient's contrast level curve is determined.

At 1222, a fallback scan prescription may be set based on user input to the adaptive scan protocol GUI. As explained above, some scan protocols may include adjustments to scan parameters such as temporal acquisition rate, and the timing of these adjustments may be based on patient-specific events that are detected. If one or more of these events are not detected, the scan prescription that is executed based on the scan protocol may not function, or may not function as intended, which may impact diagnostic image quality. Thus, to prevent such issues should the events be undetectable, a fallback scan prescription may be set that may be executed if one or more specified events cannot be detected. The adaptive scan protocol GUI may include a fallback scan prescription section where the user may specify timing and parameters of the fallback scan prescription that are not event-based, such as temporal acquisition rate changes that occur at fixed times (e.g., relative to the start of the scan).

At 1224, the information that is displayed via the adaptive scan protocol GUI may be updated as the user enters the user input described above. For example, when the user enters input adjusting a temporal acquisition rate for a particular zone, the temporal acquisition rate input for that zone may reflect the adjusted temporal acquisition rate. Further, the adaptive scan protocol GUI may include a preview section that displays a visual representation of the scan protocol, where a generic/base contrast agent curve (e.g., a VOF curve) is displayed and the timing of each scan acquisition of each zone is displayed as part of the curve. If a zone transition time is adjusted, or if a temporal acquisition rate of a zone is adjusted, the preview section may be adjusted in a corresponding manner Additional details of the adaptive scan protocol GUI, including adjustments to the preview section, are discussed below with respect to FIG. 12.

At 1226, the adaptive scan protocol is saved in memory when indicated (e.g., in response to a user input commanding the protocol be saved). The saving of the scan protocol may include saving any adjustments made to the scan protocol. The scan protocol may then be retrieved at a later time and executed in order to scan a patient according to the parameters specified in the scan protocol, as explained above with respect to FIG. 9.

Figure 13:
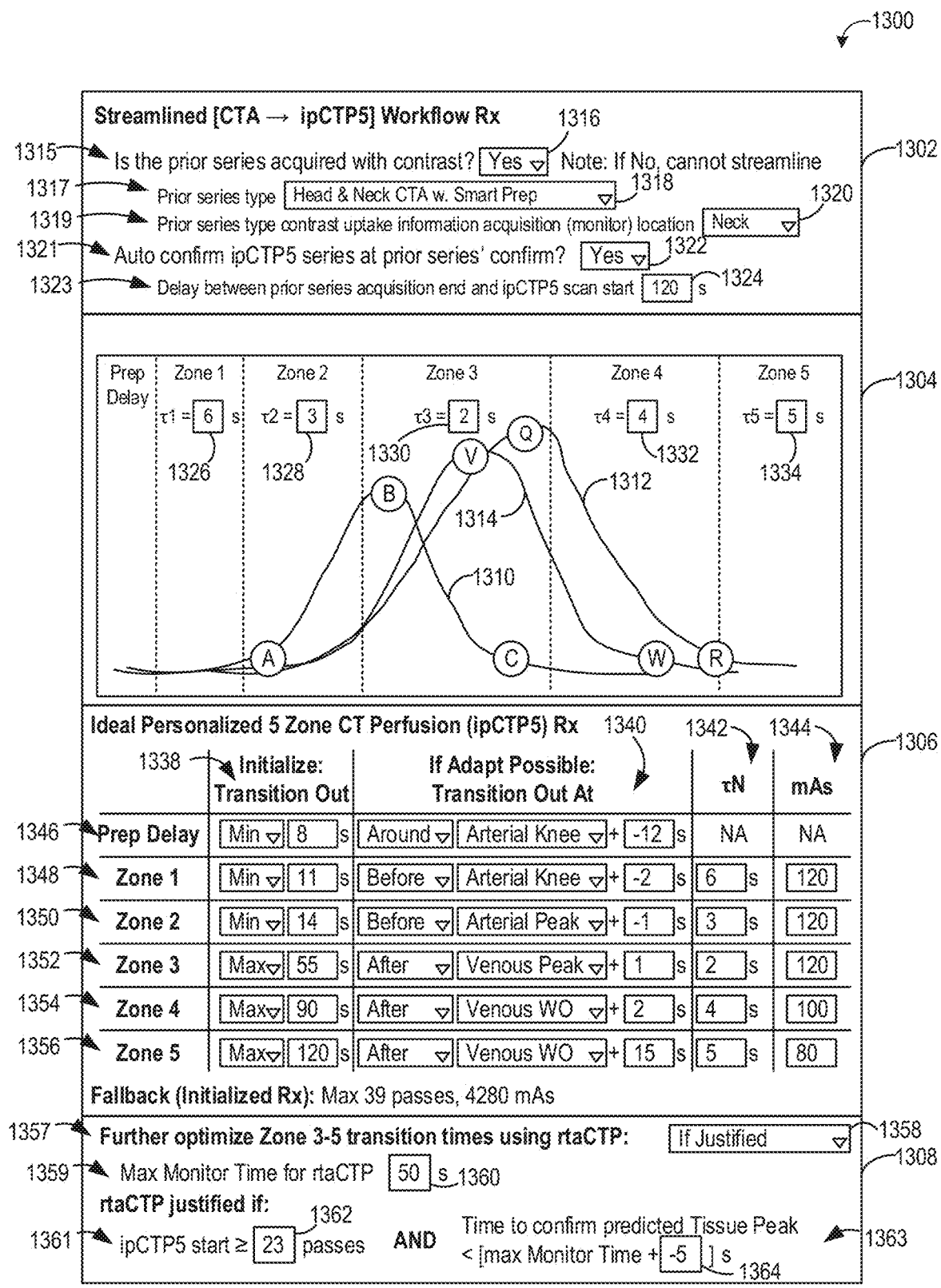
FIGS. 13-15 show an example of an adaptive scan protocol GUI, according to an embodiment of the disclosure.

Turning now to FIG. 13, an example adaptive scan protocol GUI 1300 is shown that may be displayed on a display device (e.g., display 232) in response to a user request to modify an existing adaptive scan protocol or in response to a user request to establish a new adaptive scan protocol. The user may be a lead technician or a protocol manager, for example. Adaptive scan protocol GUI 1300 is a non-limiting example of the adaptive scan protocol GUI that is displayed as part of method 1200 of FIG. 12. The adaptive scan protocol GUI 1300 shown in FIG. 13 is specific to a head perfusion scan protocol (e.g., a CTP scan), but it is to be understood that a similar adaptive scan protocol GUI may be displayed in order to set parameters for other types of contrast scans. GUI 1300 includes a linking section 1302, a preview section 1304, a prescription section 1306, and a further optimization section 1308. However, other groupings and arrangements of parameters and scan information are also possible, and the layout shown in FIG. 13 is one example of how the GUI 1300 may be arranged. The head perfusion scan protocol is shown here as an ideal personalized 5-zone CTP scan (ipCTP5) protocol, although other CTP scan protocols are also possible.

The linking section 1302 is where the user links a prior contrast series, such as a CTA, a multi-phase CTA, or a timing bolus, to the CTP scan series via a contrast series input 1315 and a prior series type input 1317. A yes option 1316 is selected (e.g., from a drop down menu) within the contrast series input 1315, indicating that the CTP scan may be optimized/streamlined using the prior contrast series. For example, as described above with respect to FIG. 9, aSP or aTB methods may be used to extrapolate AIF and VOF curves to achieve the ipCTP5 prescription personalization. A head and neck CTA with smart prep option 1318 is selected within the prior series type input 1317, although other types of contrast scans are also possible and may be included in a drop down menu. This ability to link contrast scan series enables the series to be taken in series, with the series linked to each other for timing purposes. The linking section 1302 further includes a prior series monitor location input 1319, via which the user specifies a monitor location of the prior contrast scan that will be used for personalizing the CTP scan prescription in order to calculate a relationship between the measured hemodynamics and the hemodynamics in the head (for the ipCTP5). In the example shown, a neck option 1320 is selected, which may result in different timing calculations for zone transition control points than when a head option is selected, for example. The user also selects whether the system will auto confirm the ipCTP5 series. For example, with a yes option 1322 selected, when any operator explicitly confirms the prior contrast series (e.g., the CTA) at scan time, the operator also implicitly confirms the ipCTP5 series. The linking section 1302 further includes a delay input 1323 via which the user inputs a delay parameter 1324 between the prior series (e.g., the CTA) ending and the ipCTP5 series starting. In the example shown, the delay parameter is set to 120 seconds. Thus, the system may activate the ipCTP5 series after the pre-set delay parameter (e.g., 120 seconds) has passed during scanning of a patient.

The preview section 1304 depicts a low-fidelity, generic (e.g., non-patient specific) example visual representation of an AIF curve 1310, a VOF curve 1312, and a TUC curve 1314, which may be similar to the AIF curve 602, the VOF curve 604, and the TUC curve 606 described with respect to FIG. 6, for example. The preview section 1304 may further include a plurality of lines defining boundaries between each zone of the CTP scan relative to the AIF curve 1310, the VOF curve 1312, and the TUC curve 1314. For example, each line represents a zone transition timing (e.g., a control time point), and the lines may be distributed with respect to the AIF curve 1310, the VOF curve 1312, and the TUC curve based on inputs for each zone transition that will be described below. Although five zones are shown, in other examples, GUI 1300 may display a different number of zones, such as fewer than five zones.

The preview section 1304 further includes a plurality of temporal acquisition rate inputs. That is, there is one temporal acquisition rate input for each zone to define the temporal acquisition rate, or tau value (τ) to use in that zone. A first zone (zone 1) includes a first temporal acquisition rate input 1326 for defining a first temporal acquisition rate setting (τ1) for obtaining acquisitions in the first zone, a second zone (zone 2) includes a second temporal acquisition rate input 1328 for defining a second temporal acquisition rate setting (τ2) for obtaining acquisitions in the second zone, a third zone (zone 3) includes a third temporal acquisition rate input 1330 for defining a third temporal acquisition rate setting (τ3) for obtaining acquisitions in the third zone, a fourth zone (zone 4) includes a fourth temporal acquisition rate input 1332 for defining a first temporal acquisition rate setting (τ4) for obtaining acquisitions in the fourth zone, and a fifth zone (zone 5) includes a fifth temporal acquisition rate input 1334 for defining a fifth temporal acquisition rate setting (τ5) for obtaining acquisitions in the fifth zone.

The prescription section 1306 includes a plurality of inputs for defining how the system personalizes the ipCTP5 at scan time. The five zones act as five virtual groups for the CTP, with each zone stretched or contracted to fit the hemodynamics of the particular patient being scanned. In the example shown, the prescription section 1306 uses time-based and event-driven timing to adjust the zone transition timings, which are arranged in a table. The table includes a fallback prescription column 1338, an adaptive prescription column 1340, a temporal acquisition rate (TN) column 1342 for defining the temporal acquisition of each zone, and a source current (mAs) column 1344 for defining a source current to use in each zone. The table further includes prep delay settings 1346, zone 1 settings 1348, zone 2 settings 1350, zone 3 settings 1352, zone 4 settings 1354, and zone 5 settings 1356, arranged as a plurality of inputs in each labeled row. Thus, the values input into each row define the CTA scan prescription settings for the corresponding zone (or prep delay).

At scan time, the system will be initialized to the settings input into the fallback prescription column 1338, and the CTP prescription will be updated based on data acquired during the prior contrast scan, if possible, using the settings input into the adaptive prescription column 1340. For each row, the fallback prescription column 1338 includes a relative input and a time value input for time-based timing for the zone transitions. The relative input defines whether the corresponding time value input is a minimum time value to use ("min") or a maximum time value to use ("max"), and the time value is relative a contrast agent injection time for the CTP scan. Thus, in the example shown, the fallback prescription column 1338 includes the prep delay settings 1346 initialized to transition out of the prep delay a minimum of 8 seconds after the contrast agent injection, the zone 1 settings 1348 initialized to transition out of the first zone a minimum of 11 seconds after the contrast agent injection, the zone 2 settings 1350 initialized to transition out of the second zone a minimum of 14 seconds after the contrast agent injection, the zone 3 settings 1352 initialized to transition out of the third zone a maximum of 55 seconds after the contrast agent injection, the zone 4 settings 1354 initialized to transition out of the fourth zone a maximum of 90 seconds after the contrast agent injection, and the zone 5 settings 1356 initialized to transition out of the fifth zone a maximum of 120 seconds after the contrast agent injection.

The adaptive prescription column 1340 shows how the transitions between each zone will be personalized if possible, such as described with respect to FIG. 9. Via each respective timing input, the user may specify the end time for each selected zone, where that zone transitions to the next zone. As shown, the user may directly enter a time value (e.g., 2 seconds) to each timing input, but other mechanisms for adjusting or setting a timing value are possible, such as selection from a drop-down menu, arrow inputs, etc. The time values entered may be positive or negative, which may affect whether the zone ends before or after an event specified by the corresponding event input, as described below. Each row further includes one event input for each zone. Via each respective event input, the user may specify an event that triggers the end of each selected zone, where that zone transitions to the next zone (with the time value specified in the corresponding timing input indicating when relative to the event the zone is to end). As shown, the user may select an event from a drop-down menu, but other mechanisms for specifying an event are possible, such as the user directly entering the event. The events available for selection in the drop-down menu may include venous peak, contrast agent washout (e.g., venous washout, or WO), arterial knee, arterial peak, tissue uptake peak, other contrast level curve events (such as ascent or decent knees), start of scan, and/or other events. Further, the user may select a relative timing of the event specified in the corresponding event input (e.g., around, before, or after) via a corresponding relative timing input, as will be elaborated below.

Using the values shown in FIG. 13 as an illustrative example, the adaptive prescription column 1340 specifies that the prep delay settings 1346 will be adapted to transition out of the prep delay 12 second before the arterial knee, the zone 1 settings 1348 will be adapted to transition out of the first zone 2 seconds before the arterial knee, the zone 2 settings 1350 will be adapted to transition out of the second zone 1 second before the arterial peak, the zone 3 settings 1352 will be adapted to transition out of the third zone 1 second after the venous peak, the zone 4 settings 1354 will be adapted to transition out of the fourth zone 2 seconds after the venous washout, and the zone 5 settings 1356 will be adapted to transition out of the fifth zone 15 seconds after the venous washout.

During an AIF and VOF curve estimation as the scan is performed (e.g., at 912 of FIG. 9), each event is estimated with an estimate error, resulting in an estimated time range. As one illustrative example, the arterial knee may be estimated as 20+/−2 seconds, meaning that the arterial knee is expected to occur between 18 to 22 seconds after the start of the scan. The relative timing input defines which value to use within the estimated time range. When "around" is selected as the relative timing input, 20 seconds may be used for the arterial knee timing. When "before" is selected as the relative timing input, 18 seconds may be used for the arterial knee timing. When "after" is selected as the relative timing input, 22 seconds may be used for the arterial knee timing Thus, using the example values shown in the prep delay settings 1346, the prep delay transition may be set at 8 seconds (e.g., 12 seconds subtracted from 20 seconds) for the adaptive scan prescription column 1340. Using the example values shown in the zone 1 settings 1348, the transition out of the first zone may be set at 16 seconds (e.g., 2 seconds subtracted from 18 seconds) for the adaptive scan prescription column 1340.

The value in each temporal acquisition rate input in the temporal acquisition rate column 1342 is linked to a corresponding input in the preview section 1304, such that if a value is change in the preview section 1304, the value is also changed in the linked input in the prescription section 1306 (and vice versa). For example, if the a first temporal acquisition rate input 1326 is changed to a different value (e.g., 5 seconds), the temporal acquisition rate input within the temporal acquisition rate column 1342 corresponding to the zone 1 settings 1348 also changes. Thus, either the temporal acquisition rate inputs in the preview section 1304, the temporal acquisition rate inputs in the prescription section 1306, or both may be adjusted by the user to define the temporal acquisition rate of each zone. Further, the visual representation of the zones, the generic AIF curve 1310, the generic VOF curve 1312, and the generic TUC 1314 displayed in the preview section 1304 may be updated based on input changes to both the preview section 1304 and the prescription section 1306.

In the example shown in FIG. 13, the prep delay settings 1346 do not include a temporal acquisition rate (e.g., "NA") because no acquisitions are obtained during the prep delay, the zone 1 settings 1348 include 6 seconds for the first temporal acquisition rate setting, the zone 2 settings 1350 include 3 seconds for the second temporal acquisition rate setting, the zone 3 settings 1352 include 2 seconds for the third temporal acquisition rate setting, the zone 4 settings 1354 include 4 seconds for the fourth temporal acquisition rate setting, and the zone 5 settings 1356 include 5 seconds for the fifth temporal acquisition rate setting.

The value in each source current input in the source current column 1344 defines an x-ray source (e.g., x-ray tube) current to use in each respective zone. In the example shown, the prep delay settings 1346 do not include a source current setting (e.g., "NA") because no acquisitions are obtained during the prep delay, the zone 1 settings 1348 include 120 mA for a first zone source current setting, the zone 2 settings 1350 include 120 mA for a second zone source current setting, the zone 3 settings 1352 include 120 mA for a third zone source current setting, the zone 4 settings 1354 include 100 mA for a fourth zone source current setting, and the zone 5 settings 1356 80 mA for a fifth zone source current setting. Settings for other scan parameters are possible, such as x-ray source voltage, scan start/stop locations, etc.

The further optimization section 1308 includes settings for further adapting/optimizing the CTP scan prescription (e.g., the fallback scan prescription settings given by the fallback prescription column 1338 or the personalized prescription settings given by the adaptive prescription column 1340) using real-time adaptive CTP (rtaCTP), such as described with respect to FIG. 10. The further optimization section 1308 includes a justification input 1357, via which the user may select whether to perform the rtaCTP. The justification input 1357 may include a drop-down menu via which the user may select from a plurality of options. In the example shown in FIG. 13, an if justified input 1358 is selected, meaning that the system will further optimize the CTP scan prescription during the CTP scan an associated computational cost (e.g., time impact) of performing the optimization is justified, as explained with respect to FIG. 10. Other selections will be described below with respect to FIGS. 14 and 15.

With the if justified option 1358 selected, the user may input parameters for determining whether the rtaCTP is justified, including a maximum monitor time (e.g., duration) input 1359, an ipCTP5 start input 1361, and a time to confirm predicted tissue peak input 1363. The maximum monitor time input includes a time parameter 1360, shown as 50 seconds in the example of FIG. 13. Thus, the rtaCTP protocol is set to performing monitoring for no more than 50 seconds. The ipCTP5 start input 1316 includes a number of passes parameter 1362, which is set to 23 passes in the example shown in FIG. 13. The time to confirm predicted tissue peak input 1363 includes a time parameter 1364, shown as −5 seconds in the example of FIG. 13. Thus, rtaCTP will be justified if both a tissue peak is confirmed within 45 seconds (e.g., 5 seconds before the input time parameter 1360) and the ipCTP5 start is greater than or equal to 23 passes. However, the user may set other values for the shown parameters, and the examples given are illustrative.

The values shown in FIG. 13 are illustrative, and other values may be input by the operator. However, at least in some examples, the input values may be constrained to clinically-relevant values and/or constrained relative to other values in order to prevent the user from setting up a scan protocol that will result in images having low diagnostic quality. As one example, each temporal acquisition rate may be constrained to a pre-defined allowable range for each zone, and/or the temporal acquisitions rate for each zone may be constrained relative to consecutive zones. For example, the temporal acquisition rate may be constrained to numerically decrease from zone 1 to zone 2 to zone 3, and then numerically increase from zone 3 to zone 4 to zone 5. As another example, values input into the fallback prescription column 1338 may be constrained so that the time value increases down the table (e.g., between consecutive zones). The GUI 1300 may not accept a user input that is not within the pre-determined constraints. As one example, and error message may be displayed to the user. Further, it may be understood that in response to the user updating any of the parameters/inputs shown in FIG. 13, the visual representation of the GUI 1300 may be updated to in correspondence with the adjustment.

Figure 14:
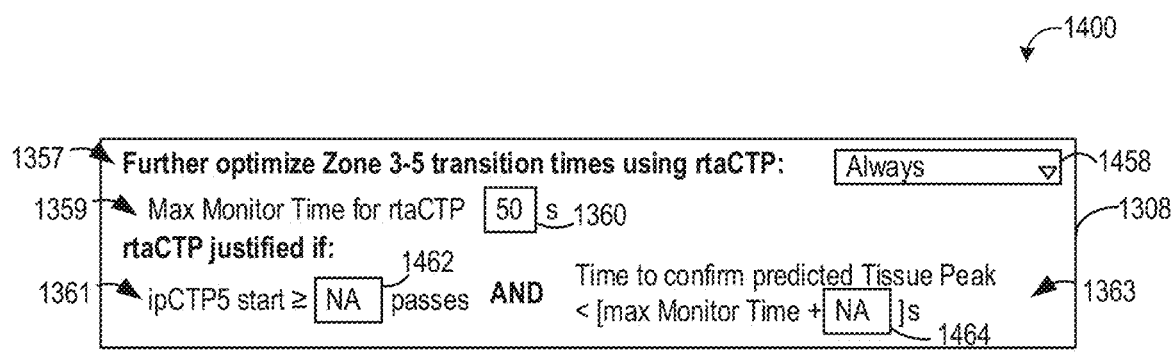

FIG. 14 shows the further optimization section 1308 of FIG. 13 in a first adjusted state 1400. Thus, aspects previously introduced in FIG. 13 are numbered the same and will not be reintroduced. In the first adjusted state 1400, an always option 1458 is selected within the justification input 1357. As a result, the rtaCTP optimization will always be performed, and the ipCTP5 input 1361 and the time to confirm predicted tissue peak input 1363 are no longer used to justify performing the rtaCTP optimization. Thus, an adjusted number of passes parameter 1462 is set to NA (e.g., not applicable), and an adjusted time parameter 1464 for the time to confirm predicted tissue peak input 1363 is set to NA. However, the time parameter 1360 of the maximum monitor time input 1359 remains set to 50 seconds, meaning that rtaCTP optimization will always be performed within the first 50 seconds of the CTP scan.

Figure 15:
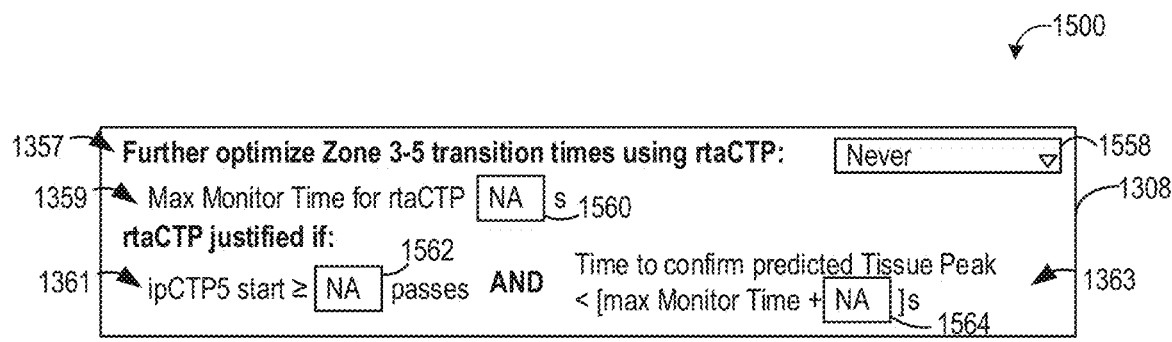

FIG. 15 shows the further optimization section 1308 of FIG. 13 in a second adjusted state 1500. Thus, aspects previously introduced in FIG. 13 are numbered the same and will not be reintroduced. In the second adjusted state 1500, a never option 1558 is selected within the justification input 1357. As a result, the rtaCTP optimization will never be performed. Thus, an adjusted time parameter 1560 of the maximum monitor time input 1359 is set to NA, an adjusted number of passes parameter 1562 is set to NA, and an adjusted time parameter 1564 for the time to confirm predicted tissue peak input 1363 is set to NA.

Next, FIG. 16 shows an example run-time GUI 1600 that may be displayed on a display device (e.g., the display 232 of FIG. 2) in response to a user request to execute an existing adaptive scan protocol. The run-time GUI 1600 is a non-limiting example of the run-time GUI that is displayed as part of method 900 of FIG. 9 and/or method 1000 of FIG. 10, for example.

Run-time GUI 1600 includes a scan prescription section 1610 where a visual representation of a CTP scan prescription for the imaging subject (e.g., patient) is displayed. The scan prescription section 1610 may be a replicate of the GUI 1300 of FIG. 13 for example. Thus, the adaptive scan protocol GUI used to define a preset protocol may be displayed within the run-time GUI 1600 for additional adjustments at run-time, if desired. For example, the operator is given the opportunity to confirm the settings for the current adaptive scan protocol, and if desired, change the settings. The scan prescription section, which may include any or all of the features described above with respect to FIGS. 7-10 and may function as previously includes a linking section 1602, a preview section 1604, a prescription section 1606, and a further optimization section 1608, which may include any or all of the features described above with respect to FIGS. 13-15. As such, the scan prescription may be generated based on the selected adaptive scan protocol and the settings input into the scan prescription section 1610 ahead of time and/or at the scan time.

While the preview section 1604 shown in FIG. 16 includes the same generic AIF curve, VOF curve, and TUC shown in the adaptive scan protocol GUI described with respect to FIG. 13, it is to be understood that at least in some examples, the run-time GUI 1600 may display a visual representation of the scan prescription that has been generated based on the patient's actual measured AIF signal, for example. As such, the preview section 1604 may be updated as patient-specific data become available. The patient-specific data may be obtained from a prior contrast scan, a timing bolus carried out before the current contrast scan, or during the current contrast scan. In another example, the preview section 1604 may initially display a fallback scan prescription, which may be based on the fallback scan protocol as described above, and may not be based on patient information. Then, once the patient-specific data are generated, the fallback scan prescription may be replaced with the personalized curves.

The run-time GUI 1600 also includes a first progress bar 1620 and a second progress bar 1622 that each display the current status/progress of the contrast scan with respect to time. As the contrast scan progresses, the first progress bar 1620 and the second progress bar 1622 may change in visual appearance. For example, the first progress bar 1620 may represent a CTA scan, as shown, and may include a waveform. As the scan progresses, the color of the waveform may progressively change, e.g., turning gray to blue from left to right, in sync with the scan progress. The second progress bar 1622 may represent an ipCTP5 scan, as shown, and the color of the second progress bar 1622 may progressively change in sync with the scan progression.

Additionally, the run-time GUI 1600 may include a patient information section 1630, a scan information section 1640, a scan range selection section 1650, a settings section 1605, and a dose information section 1660. In the patient information section 1630, information about the imaging subject may be displayed, such as a patient name and/or ID number, patient gender, and patient position (e.g., head first/supine). In the scan information section 1640, information about the scan protocol may be displayed, such as the name of the scan protocol and the sequences of the scan protocol (e.g., the scout scan, non-contrast scan, and contrast scan or scans, which includes a CTA and an ipCTP5 in the example shown in FIG. 16). Additionally, when a sequence of the scan protocol is completed, a checkmark or other visual indicator may be displayed. The current sequence may be highlighted or otherwise visually indicated. In the dose information section 1660, information about the x-ray radiation dose administered to the imaging subject may be displayed, such as projected dose, total accumulated dose, etc., so that the operator of the imaging system may monitor the patient's x-ray radiation exposure.

In the scan range selection section 1650, scout images of the imaging subject may be displayed with the current scan range displayed as an overlay on the scout image(s). As another example, when scout images are not available, the scan range may be displayed as an overlay on a generic image of a similar scan (e.g., same patient orientation) that is not specific to the imaging subject. The scan range may be adjusted by adjusting the size and/or position of the overlay. In the settings section 1605, the operator may define the start location of the scan, the end location of the scan, a range of the scan, a number of images to acquire, the anatomy being imaged, and other anatomy selection settings. The operator may further select settings related to a current and/or voltage of an x-ray source used, contrast settings, scan type settings, and timing settings. The settings may be pre-filled based on a selected pre-defined protocol and/or adjusted by the operator at run-time.

Further, the run-time GUI 1600 may include one or more user interface inputs that, when selected by the operator, confirm the scan protocol setting and/or trigger the start of the contrast scan. In the example shown, the run-time GUI 1600 includes a confirm settings input 1665, which may trigger the start of the contrast scan. In some examples, the operator may not make adjustments to the scan settings (e.g., in the settings section 1605 and the scan prescription section 1610), enabling the operator to start the scan via the confirm settings input 1665 without performing additional protocol set-up. Thus, the run-time GUI 1600 enables the operator to begin the scan via a single selection of the confirm settings input 1665, if desired. As such, the run-time GUI 1600 provides a technical solution for reducing a cognitive load on the operator at scan time and reducing an amount of time before the scan is commenced. Further, the run-time GUI 1600 is shown including a done scanning input 1670, which may trigger the end of the contrast scan and save all acquired data and parameter settings to a unique file.

Thus, the systems and methods disclosed herein provide for estimating when various contrast agent time points/curves will occur for a specific patient, using (at least initially) a short measured segment (referred to as a contrast signal) of a contrast enhancement curve measured at a monitoring area as an input to a machine learning model to predict the remaining contrast agent time points or curves. The contrast enhancement curve may be an arterial inflow function (AIF) curve, and the segment of the AIF curve may be measured at an artery of the patient, in an example. In another example, the contrast enhancement curve may be a venous outflow function (VOF) curve, and the segment of the VOF curve may be measured at a vein of the patient. In a still further example, the contrast enhancement curve may be a tissue uptake curve (TUC), and the segment may be measured at a tissue of interest (e.g., the brain), where the tissue is segmented in a plurality of images. In some examples, more than one contrast enhancement curve may be measured (e.g., both the AIF and the VOF may be measured). Based on these estimated time points, various contrast scan actions may be carried out. As explained above with respect to FIG. 9, the predicted time points may be used to generate a personalized five-zone CTP scan prescription, which may be further adapted in-flight, as explained above with respect to FIG. 10. The five-zone CTP scan prescription may be carried out with a second contrast injection following a first contrast injection, and the time points may be estimated using a measured segment of a contrast enhancement curve of the first contrast injection. If a personalized prescription cannot be generated, a fallback prescription is performed, which serves as a default scan prescription for initializing the scan.

The time points may be estimated from an AIF signal or a TUC signal. As explained above with respect to FIGS. 3-8, the AIF signal may be a segment of an AIF curve measured at an arterial ROI and the TUC signal may be a segment of a TUC measured at a segmented tissue region. Each estimation method includes a model. In the training for the models, if the AIF segment is the input, the measured signal for training the model is the AIF curve segment and/or features from the AIF curve segment. The ground truth for training the model may be the collection of times for A, B, C, P, Q, and R on the AIF and VOF curves and possibly HU values as well. If the TUC segment is the input, the measured signal for training the model is the TUC curve segment and/or features from the TUC curve segment. The ground truth for training may be same as above (e.g., A, B, C, P, Q, and R times and possibly HU values as well).

Further, the systems and methods disclosed herein provide for workflows for setting adaptive scan protocols and then executing the adaptive scan protocols, with each workflow including a graphical user interface via which a respective user (e.g., lead technologist and then scanning technologist) may adjust/set and then carry out an adaptive scan protocol. The adaptive scan protocol GUI described herein may allow a lead technologist or another supervising clinician/personnel to quickly set parameters for the scan protocol based on patient events that will be determined at the time of scanning. The adaptive scan protocol GUI may provide the user with a plurality of options for setting the parameters for the scan protocol, such as a number of zones (e.g., 1-5 or other suitable range), a limited set of scan parameters that can be adjusted for each zone (such as temporal acquisition rate and x-ray source current), and events that can trigger the end of each zone. In doing so, user interaction with the computing device to set the adaptive scan protocol at scan time may be reduced, thereby making the user's workflow more efficient. Further, consistency may be increased all adaptive scan protocols.

A technical effect of the disclosure is that an adaptive, personalized multiple zone perfusion scan may be performed, which may increase diagnostic image quality and/or reduce patient radiation exposure, while a general prescription is used when a personalized multiple zone perfusion scan prescription cannot be generated. Another technical effect of the disclosure is that an adaptive contrast scan may be defined and performed based on patient specific events, which may increase diagnostic image quality and/or reduce user workflow demands.

In an embodiment, a method comprises: processing acquired projection data of a monitoring area of a subject to measure a first contrast signal of a contrast agent administered to the subject via a first injection; initializing a contrast scan of the subject according to a fallback scan prescription; determining when each of a plurality of zones of the contrast scan are estimated to occur based on the contrast signal; generating a personalized scan prescription for the contrast scan based on when each of the plurality of zones are estimated to occur; and performing the contrast scan according to the personalized scan prescription after a second injection of the contrast agent. In a first example of the method, consecutive zones of the plurality of zones differ in in one or more of a temporal acquisition rate, a tube current, and a number of exposures. In a second example of the method, which optionally includes the first example, determining when each of the plurality of zones of the scan protocol are estimated to occur based on the contrast signal comprises determining a plurality of estimated control time points, including an estimated first control time point for when a first zone is estimated to transition to a second zone, an estimated second control time point for when the second zone is estimated to transition to a third zone, an estimated third control time point for when the third zone is estimated to transition to a fourth zone, an estimated fourth control time point for when the fourth zone is estimated to transition to a fifth zone, and an estimated fifth control time point for when the fifth zone is estimated to end. In a third example of the method, which optionally includes one or both of the first and second examples, wherein the plurality of estimated control time points are estimated from an arterial inflow function (AIF) curve and a venous outflow function (VOF) curve output from a machine learning model, where the first contrast signal is entered as input to the machine learning model. In a fourth example of the method, which optionally includes one or more or each of the first through third examples, generating the scan prescription includes setting one or more scan parameters for each zone. In a fifth example of the method, which optionally includes one or more or each of the first through fourth examples, setting the one or more scan parameters for each zone comprises setting a first control time point for transitioning from the first zone to the second zone to the estimated first control time point, setting a second control time point for transitioning form the second zone to the third zone to the estimated second control time point, setting a third control time point for transitioning from the third zone to the fourth zone to the estimated third control time point, setting a fourth control time point for transitioning from the fourth zone to the fifth zone to the estimated fourth control time point, and setting a fifth control time point for ending the fifth zone to the estimated fifth control time point. A sixth example of the method optionally includes one or more or each of the first through fifth examples and further comprises while performing the contrast scan according to the personalized scan prescription, identifying a peak in a second contrast signal measured during the contrast scan within a predetermined time frame; if the peak is identified within the predetermined time frame, updating the personalized scan prescription to generate an adapted scan prescription for the contrast scan based on the second contrast signal, and performing a remainder of the contrast scan according to the adapted scan prescription; and if the peak in the second contrast signal is not identified within the predetermined time frame, continuing the remainder of the contrast scan according to the personalized scan prescription. In a seventh example of the method, which optionally includes one or more or each of the first through sixth examples, the second contrast signal is a tissue uptake curve (TUC), and the peak a global peak of the TUC. In an eighth example of the method, which optionally includes one or more or each of the first through seventh examples, updating the personalized scan prescription to generate the adapted scan prescription for the contrast scan based on the second contrast signal comprises adjusting one or more of the third control time point, the fourth control time point, and the fifth control time point.

In another embodiment, a method for an imaging system comprises: during a first contrast scan, processing acquired projection data of a monitoring area of a subject to measure a contrast signal of a contrast agent administered to the subject via a first injection; initializing a second contrast scan to a fallback prescription; while operating with a first condition, estimating a plurality of transition times between a plurality of zones of the second contrast based on the contrast signal and performing the second contrast scan according to a personalized scan prescription generated using the plurality of estimated transition times; and while operating with a second condition, and performing the second contrast scan according to the fallback prescription. In a first example of the method, the first condition includes successfully estimating an arterial inflow function (AIF) curve and a venous outflow function (VOF) curve via a machine learning model, and the second condition includes not successfully estimating the AIF curve and the VOF curve. In a second example of the method, which optionally includes the first example, each of the plurality zones defines a time range for operating at a zone-specific acquisition rate. A third example of the method optionally includes one or both of the first and second examples and further comprises, while performing a first portion of the second contrast scan after administering a second injection of the contrast agent to the subject, further adjusting parameters for a second portion of the second contrast scan responsive to justification conditions being met. In a fourth example of the method, which optionally includes one or more or each of the first through third examples, the plurality of zones comprises a first zone followed by a second zone, a third zone following the second zone, a fourth zone following the third zone, and a fifth zone following the second zone, and performing the first portion of the second contrast scan includes performing acquisitions during the first zone and the second zone. In a fifth example of the method, which optionally includes one or more or each of the first through fourth examples, further adjusting the parameters for the second portion of the second contrast can responsive to conditions being met comprises adjusting a third transition time between the third zone and the fourth zone, adjusting a fourth transition time between the fourth zone and the third zone, and adjusting an ending time of the fifth zone based on a tissue uptake curve measured during the first portion of the second contrast scan. In a sixth example of the method, which optionally includes one or more or each of the first through fifth examples, the justification conditions include identifying a peak in the tissue uptake curve within a threshold duration since the second injection.

In yet another embodiment, a system comprises: an x-ray source that emits a beam of x-rays toward a subject to be imaged; a detector that receives the x-rays attenuated by the subject; a data acquisition system (DAS) operably connected to the detector; and a computer operably connected to the DAS and configured with instructions in non-transitory memory that when executed cause the computer to: initialize a perfusion scan of an anatomical region of interest (ROI) of the subject according to a first scan prescription; process projection data from the DAS during a portion of the perfusion scan to measure a contrast signal of the contrast agent; identify a peak in the contrast signal prior to a threshold time; if the peak in the contrast signal is identified within the threshold time, perform a remainder of the perfusion scan according to an adapted scan prescription that is dependent on the contrast signal; and if the peak in the contrast signal is not identified prior to the threshold time, complete the remainder of the perfusion scan according to the first scan prescription, where the first scan prescription is independent of the contrast signal measured during the perfusion scan. In a first example of the system, the first scan prescription is one of a personalized scan prescription generated based on acquisitions obtained during a prior contrast scan of the subject or a fallback scan prescription that is not based on any prior contrast scan of the subject. In a second example of the system, which optionally includes the first example, the perfusion scan includes a plurality of zones, each of the plurality of zones including an associated temporal acquisition frequency, and the personalized scan prescription includes a transition into a zone having a highest temporal acquisition frequency at a later time than the fallback prescription and a transition out of the zone having the highest temporal acquisition frequency at an earlier time than the fallback prescription. In a third example of the system, which optionally includes one or both of the first and second examples, the adapted scan prescription includes a transition to a higher temporal acquisition frequency at a first time point that is based on the contrast signal and the first scan prescription includes the transition to the higher frequency temporal acquisition frequency at a second time point that is independent of the contrast signal.

In another representation, a method for a computing device communicatively coupled to an imaging system comprises: receiving a selection of a multi-zone perfusion scan protocol; displaying an adaptive scan protocol graphical user interface (GUI) on a display device coupled to the computing device; adjusting one or more zone parameters of the multi-zone perfusion scan protocol in response to user input to the adaptive scan protocol GUI; updating a visual representation of the multi-zone perfusion scan protocol displayed via the adaptive scan protocol GUI in correspondence to the adjustment of the one or more zone parameters of the multi-zone perfusion scan protocol; and storing the adjusted multi-zone perfusion scan protocol in a memory of the computing device. In a first example, the method further comprises setting a scan prescription for the imaging system based on the adjusted multi-zone perfusion scan protocol and a contrast signal measured from a patient and performing one or more acquisitions with the imaging system according to the scan prescription. In a second example, which optionally includes the first example, the method further comprises displaying, on the display device, a run-time GUI in response to a request to execute the adjusted multi-zone perfusion scan protocol, the run-time GUI including a visual representation of the scan prescription. In a third example of the method, which optionally includes one or both of the first and second examples, adjusting the one or more parameters of the multi-zone perfusion scan protocol comprises adjusting a temporal acquisition rate of at least one zone of the multi-zone perfusion scan and/or a timing of the at least one zone of the multi-zone perfusion scan in response to user input to the adaptive scan protocol GUI. In a fourth example of the method, which optionally includes one or more or each of the first through third examples, adjusting the temporal acquisition rate of the at least one zone and/or the timing of the at least one zone in response to user input to the adaptive scan protocol GUI comprises: displaying, via the adaptive scan protocol GUI, a respective timing input for each zone and a respective event input for each zone; and adjusting the timing of the at least one zone by adjusting a time value of the respective timing input for the at least one zone and/or adjusting a selected event of the respective event input for the at least one zone. In a fifth example of the method, which optionally includes one or more or each of the first through fourth examples, the respective event input includes a drop-down menu including a plurality of possible events, the plurality of possible events including an arterial knee of a patient arterial input function curve, an arterial peak of the patient arterial input function curve, a venous peak of a patient venous output function curve, and a venous washout of the patient venous output function curve. In a sixth example of the method, which optionally includes one or more or each of the first through fifth examples, the visual representation of the multi-zone perfusion scan protocol includes a plurality of generic patient contrast level curves and a plurality of transition timings between each zone of the multi-zone perfusion scan, and wherein the plurality of transition timings are distributed based on selected inputs for each of the plurality of transition timings. In a seventh example of the method, which optionally includes one or more or each of the first through sixth examples, updating the visual representation of the multi-zone perfusion scan protocol displayed via the adaptive scan protocol GUI in correspondence to the adjustment of the one or more parameters of the multi-zone perfusion scan protocol comprises updating the distribution of the plurality of transition timings in response to an adjustment to at least one of the selected inputs for each of the plurality of transition timings. In an eighth example of the method, which optionally includes one or more or each of the first through seventh examples, the visual representation of the multi-zone perfusion scan protocol includes a table relating parameter settings for a fallback prescription and an adaptive prescription for each zone of the multi-zone perfusion scan protocol. In a ninth example of the method, which optionally includes one or more or each of the first through eighth examples, the visual representation of the multi-zone perfusion scan protocol includes a real-time adaptive prescription section, and wherein updating the visual representation of the multi-zone perfusion scan protocol displayed via the adaptive scan protocol GUI in correspondence to the adjustment of the one or more parameters of the multi-zone perfusion scan protocol comprises updating justification setting parameters responsive to adjustment of a justification input.

In yet another representation, a method for a computing device communicatively coupled to an imaging system comprises: setting a scan prescription for imaging a patient with the imaging system based on a scan protocol and a measured contrast signal of the patient during a prior contrast scan; displaying, on a display device coupled to the computing device, a run-time graphical user interface (GUI), the run-time GUI including a visual representation of the scan prescription; performing one or more acquisitions with the imaging system according to the scan prescription; further adjusting the scan prescription based measurements determined from the one or more acquisitions; and updating the visual representation of the scan prescription displayed via the run-time GUI. In a first example of the method, the visual representation of the scan prescription comprises a plurality of control time points displayed with respect to at least one contrast signal curve, and the plurality of control time points are distributed based on a respective transition time setting of each of one or more zones of the scan protocol. In a second example of the method, which optionally includes the first example, the at least one contrast level curve is updated after at least one acquisition of the one or more acquisitions has been performed. In a third example of the method, which optionally includes one or both of the first and second examples, the scan prescription is a perfusion scan prescription, and the prior contrast scan is one of a timing bolus and an angiography scan.

In still another representation, a system comprises: a display device; a non-transitory memory storing instructions; and a processor configured to execute the instructions to: select a scan protocol; display, on the display device, an adaptive scan protocol graphical user interface (GUI); adjust one or more parameters of the scan protocol in response to user input to the adaptive scan protocol GUI; update a visual representation of the scan protocol displayed via the adaptive scan protocol GUI in correspondence to the adjustment of the one or more parameters of the scan protocol; store the adjusted scan protocol in the non-transitory memory; display, on the display device, a run-time GUI including a visual representation of a scan prescription generated based on the adjusted scan protocol and at least one contrast signal measured from a patient; and command an imaging system to perform one or more acquisitions of a monitoring region of the patient according to the scan prescription. In a first example of the system, the scan protocol includes performing acquisitions throughout a plurality of timing zones, and wherein the one or more parameters of the scan protocol comprise a temporal acquisition rate for each of the plurality of timing zones and/or a timing for each of the plurality of timing zones. In a second example of the system, which optionally includes the first example, the timing of each of the plurality of timing zones is relative to one or more events. In a third example of the system, which optionally includes one or both of the first and second examples, the one or more events include an arterial knee of an arterial input function curve determined from the at least one contrast signal measured from the patient, an arterial peak of the determined arterial input function curve determined from the at least one contrast signal, a venous peak of a venous output function curve determined from the at least one contrast signal measured from the patient, and a venous washout of the determined venous output function curve. In a fourth example of the system, which optionally includes one or more or each of the first through third examples, the visual representation of the scan protocol displayed via the adaptive scan protocol GUI includes first group of parameters defining a fallback scan prescription and a second group of parameters defining a personalized scan prescription. In a fifth example of the system, which optionally includes one or more or each of the first through fourth examples, the first group of parameters defining the fallback scan prescription include time-based timing parameters for prescribing the timing for each of the plurality of timing zones and the second group of parameters defining the personalized scan prescription include event-based timing parameters for prescribing the timing for each of the plurality of timing zones.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

The invention claimed is:
1. A method, comprising:
processing acquired projection data of a monitoring area of a subject to measure a first contrast signal of a contrast agent administered to the subject via a first injection;
initializing a contrast scan of the subject according to a fallback scan prescription comprising control points each defining a timing of transitioning between a plurality of zones of the contrast scan, each of the plurality of zones having a defined temporal acquisition rate setting;
determining when each of the plurality of zones of the contrast scan are estimated to occur based on the first contrast signal;
generating a personalized scan prescription for the contrast scan based on when each of the plurality of zones are estimated to occur; and
performing the contrast scan according to the personalized scan prescription after a second injection of the contrast agent.

2. The method of claim 1, wherein consecutive zones of the plurality of zones differ in in one or more of the defined temporal acquisition rate setting, a tube current, and a number of exposures.

3. The method of claim 1, wherein determining when each of the plurality of zones of the contrast scan are estimated to occur based on the first contrast signal comprises determining a plurality of estimated control time points, including an estimated first control time point for when a first zone is estimated to transition to a second zone, an estimated second control time point for when the second zone is estimated to transition to a third zone, an estimated third control time point for when the third zone is estimated to transition to a fourth zone, an estimated fourth control time point for when the fourth zone is estimated to transition to a fifth zone, and an estimated fifth control time point for when the fifth zone is estimated to end.

4. The method of claim 3, wherein the plurality of estimated control time points is estimated from an arterial inflow function (AIF) curve and a venous outflow function (VOF) curve output from a machine learning model, where the first contrast signal is entered as input to the machine learning model.

5. The method of claim 3, wherein generating the personalized scan prescription includes setting one or more scan parameters for each of the plurality of zones.

6. The method of claim 5, wherein setting the one or more scan parameters for each of the plurality of zones comprises setting a first control time point for transitioning from the first zone to the second zone to the estimated first control time point, setting a second control time point for transitioning form the second zone to the third zone to the estimated second control time point, setting a third control time point for transitioning from the third zone to the fourth zone to the estimated third control time point, setting a fourth control time point for transitioning from the fourth zone to the fifth zone to the estimated fourth control time point, and setting a fifth control time point for ending the fifth zone to the estimated fifth control time point.

7. The method of claim 6, further comprising:
while performing the contrast scan according to the personalized scan prescription, identifying a peak in a second contrast signal measured during the contrast scan within a predetermined time frame;
if the peak is identified within the predetermined time frame, updating the personalized scan prescription to generate an adapted scan prescription for the contrast scan based on the second contrast signal, and performing a remainder of the contrast scan according to the adapted scan prescription; and
if the peak in the second contrast signal is not identified within the predetermined time frame, continuing the remainder of the contrast scan according to the personalized scan prescription.

8. The method of claim 7, wherein the second contrast signal is a tissue uptake curve (TUC), and the peak is a global peak of the TUC.

9. The method of claim 7, wherein updating the personalized scan prescription to generate the adapted scan prescription for the contrast scan based on the second contrast signal comprises adjusting one or more of the third control time point, the fourth control time point, and the fifth control time point.

10. A method for an imaging system, comprising:
during a first contrast scan, processing acquired projection data of a monitoring area of a subject to measure a contrast signal of a contrast agent administered to the subject via a first injection;
initializing a second contrast scan to a fallback prescription;
while operating with a first condition that includes successfully estimating an arterial inflow function (AIF) curve and a venous outflow function (VOF) curve via a machine learning model, estimating a plurality of transition times between a plurality of zones of the second contrast scan based on the contrast signal and performing the second contrast scan according to a personalized scan prescription generated using the plurality of estimated transition times; and
while operating with a second condition that includes not successfully estimating the AIF curve and the VOF curve, and performing the second contrast scan according to the fallback prescription.

11. The method of claim 10, wherein each of the plurality of zones defines a time range for operating at a zone-specific acquisition rate.

12. The method of claim 10, further comprising:
while performing a first portion of the second contrast scan after administering a second injection of the contrast agent to the subject, further adjusting parameters for a second portion of the second contrast scan responsive to justification conditions being met.

13. The method of claim 12, wherein the plurality of zones comprises a first zone followed by a second zone, a third zone following the second zone, a fourth zone following the third zone, and a fifth zone following the second zone, and performing the first portion of the second contrast scan includes performing acquisitions during the first zone and the second zone.

14. The method of claim 13, wherein further adjusting the parameters for the second portion of the second contrast scan responsive to conditions being met comprises adjusting a third transition time between the third zone and the fourth zone, adjusting a fourth transition time between the fourth zone and the third zone, and adjusting an ending time of the fifth zone based on a tissue uptake curve measured during the first portion of the second contrast scan.

15. The method of claim 14, wherein the justification conditions include identifying a peak in the tissue uptake curve within a threshold duration since the second injection.

16. A system, comprising:
an x-ray source that emits a beam of x-rays toward a subject to be imaged;
a detector that receives the x-rays attenuated by the subject;
a data acquisition system (DAS) operably connected to the detector; and
a computer operably connected to the DAS and configured with instructions in non-transitory memory that when executed cause the computer to:
initialize a perfusion scan of an anatomical region of interest (ROI) of the subject according to a first scan prescription;
process projection data from the DAS during a portion of the perfusion scan to measure a contrast signal of a contrast agent;
identify a peak in the contrast signal prior to a threshold time;
if the peak in the contrast signal is identified within the threshold time, perform a remainder of the perfusion scan according to an adapted scan prescription that is dependent on the contrast signal; and if the peak in the contrast signal is not identified prior to the threshold time, complete the remainder of the perfusion scan according to the first scan prescription, where the first scan prescription is independent of the contrast signal measured during the perfusion scan.

17. The system of claim 16, wherein the first scan prescription is one of a personalized scan prescription generated based on acquisitions obtained during a prior contrast scan of the subject or a fallback scan prescription that is not based on any prior contrast scan of the subject.

18. The system of claim 17, wherein the perfusion scan includes a plurality of zones, each of the plurality of zones including an associated temporal acquisition frequency, and the personalized scan prescription includes a transition into a zone having a highest temporal acquisition frequency at a later time than the fallback scan prescription and a transition out of the zone having the highest temporal acquisition frequency at an earlier time than the fallback scan prescription.

19. The system of claim 16, wherein the adapted scan prescription includes a transition to a higher temporal acquisition frequency at a first time point that is based on the contrast signal and the first scan prescription includes the transition to the higher temporal acquisition frequency at a second time point that is independent of the contrast signal.

\* \* \* \* \*